United States Patent [19]
Cook et al.

[11] Patent Number: 6,020,328
[45] Date of Patent: Feb. 1, 2000

[54] 20-KETO-11β-ARYLSTEROIDS AND THEIR DERIVATIVES HAVING AGONIST OR ANTAGONIST HORMONAL PROPERTIES

[75] Inventors: C. Edgar Cook, Staunton, Va.; John A. Kepler, Raleigh, N.C.; Ping-sheng Zhang, Millbrae, Calif.; Yue-wei Lee, Chapel Hill; C. Ray Tallent, Raleigh, both of N.C.

[73] Assignee: Research Triangle Institute, Research Triangle Park, N.C.

[21] Appl. No.: 09/035,949

[22] Filed: Mar. 6, 1998

[51] Int. Cl.$^7$ .............................. A61K 31/58; C07J 43/00
[52] U.S. Cl. ..................... 514/176; 540/107; 540/108; 514/841; 514/843
[58] Field of Search ..................... 540/107, 108; 514/176, 841, 843

[56] References Cited

U.S. PATENT DOCUMENTS

| | | | |
|---|---|---|---|
| 4,386,085 | 5/1983 | Teutsch et al. | 424/238 |
| 4,447,424 | 5/1984 | Teutsch et al. | |
| 4,609,651 | 9/1986 | Rohde et al. | |
| 4,774,236 | 9/1988 | Cook et al. | |
| 4,861,763 | 8/1989 | Cook et al. | |
| 4,871,724 | 10/1989 | Groen et al. | |
| 4,874,754 | 10/1989 | Nique et al. | |
| 4,900,725 | 2/1990 | Nioue et al. | |
| 4,954,490 | 9/1990 | Cook et al. | |
| 5,073,548 | 12/1991 | Cook et al. | |
| 5,446,036 | 8/1995 | Scholz et al. | 514/175 |

FOREIGN PATENT DOCUMENTS

| | | |
|---|---|---|
| 0 057 115 | 8/1982 | European Pat. Off. |
| 0 116 974 | 8/1984 | European Pat. Off. |
| 0 147 361 | 7/1985 | European Pat. Off. |
| 0 190 759 | 8/1986 | European Pat. Off. |
| 0 192 598 | 8/1986 | European Pat. Off. |
| 0 245 170 | 11/1987 | European Pat. Off. |
| 0 254 670 | 1/1988 | European Pat. Off. |
| 0 277 089 | 8/1988 | European Pat. Off. |
| 0 277 676 | 8/1988 | European Pat. Off. |
| 0 289 073 | 11/1988 | European Pat. Off. |
| 0 305 242 | 3/1989 | European Pat. Off. |
| 0 321 010 | 6/1989 | European Pat. Off. |
| 0 349 481 | 1/1990 | European Pat. Off. |
| 0 404 283 | 12/1990 | European Pat. Off. |
| 0 411 733 | 2/1991 | European Pat. Off. |
| 0 549 041 | 6/1993 | European Pat. Off. |
| 287 510 | 2/1991 | Germany. |
| 289 539 | 5/1991 | Germany. |
| 290 198 | 5/1991 | Germany. |
| WO 87/05908 | 10/1987 | WIPO. |
| WO 88/01868 | 3/1988 | WIPO. |
| WO 89/12448 | 12/1989 | WIPO. |
| WO 92/11279 | 7/1992 | WIPO. |
| WO 93/17686 | 9/1993 | WIPO. |
| WO 93/21926 | 11/1993 | WIPO. |
| WO 96/30390 | 10/1996 | WIPO. |
| WO 97/41145 | 11/1997 | WIPO. |

OTHER PUBLICATIONS

Chemical Abstract, AN 78501u, EP 299,913, Jan. 18, 1989.
Chemical Abstract, AN 6285s, FR 2,586,021, Feb. 13, 1987.
Chemical Abstract, AN 154227b, EP 308,345, Mar. 22, 1989.
Chemical Abstract, AN 164959b, EP 310,542, Apr. 5, 1989.
Chemical Abstract, AN 132580a, EP 369,881, May 23, 1990.
Chemical Abstract, AN 93429d, DE 3,621,024, Dec. 23, 1987.
Patent Abstract of US 4,477,445, Oct. 16, 1994.
G. Teutsch, et al., Human Reproduction, vol. 9, Supplement 1, pp. 12 to 31, "History and Perspectives of Antiprogestins from the Chemist s Point of View", 1994.
C. E. Cook, et al., Human Reproduction, vol. 9, Supplement 1, pp. 32 to 39, "Effects of D–Ring Substituents on Antiprogestational (Antagonist) and Progestational (Agonist) Activity of 11β–aryl steroids", 1994.
M. J. van den Heuvel, et al., Recueil des Travaux Chimiques des Pays–Bas., vol. 112, No. 02, pp. 107 to 112, "Synthesis of 6β–Methyl Analogues of Mifepristone, New Selective Antiprogestagens", 1993.

*Primary Examiner*—Jose' G. Dees
*Assistant Examiner*—Barbara Badio
*Attorney, Agent, or Firm*—Oblon, Spivak, McClelland, Maier & Neustadt, P.C.

[57] ABSTRACT

The invention is directed to 20-keto-11β-arylsteroids of formula I:

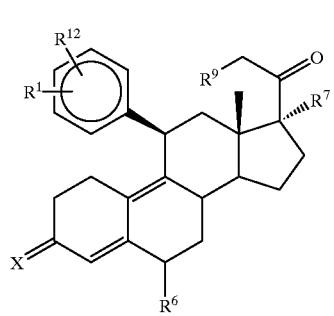

(I)

wherein $R^1$, $R^6$, $R^7$, $R^9$, $R^{12}$ and X are as defined by the specification. The compounds exhibit progestational and antiprogestational activities.

9 Claims, 10 Drawing Sheets

Chart A - Synthesis of 17α-Reversed Analogs

Chart B - Synthesis of Spirolactones

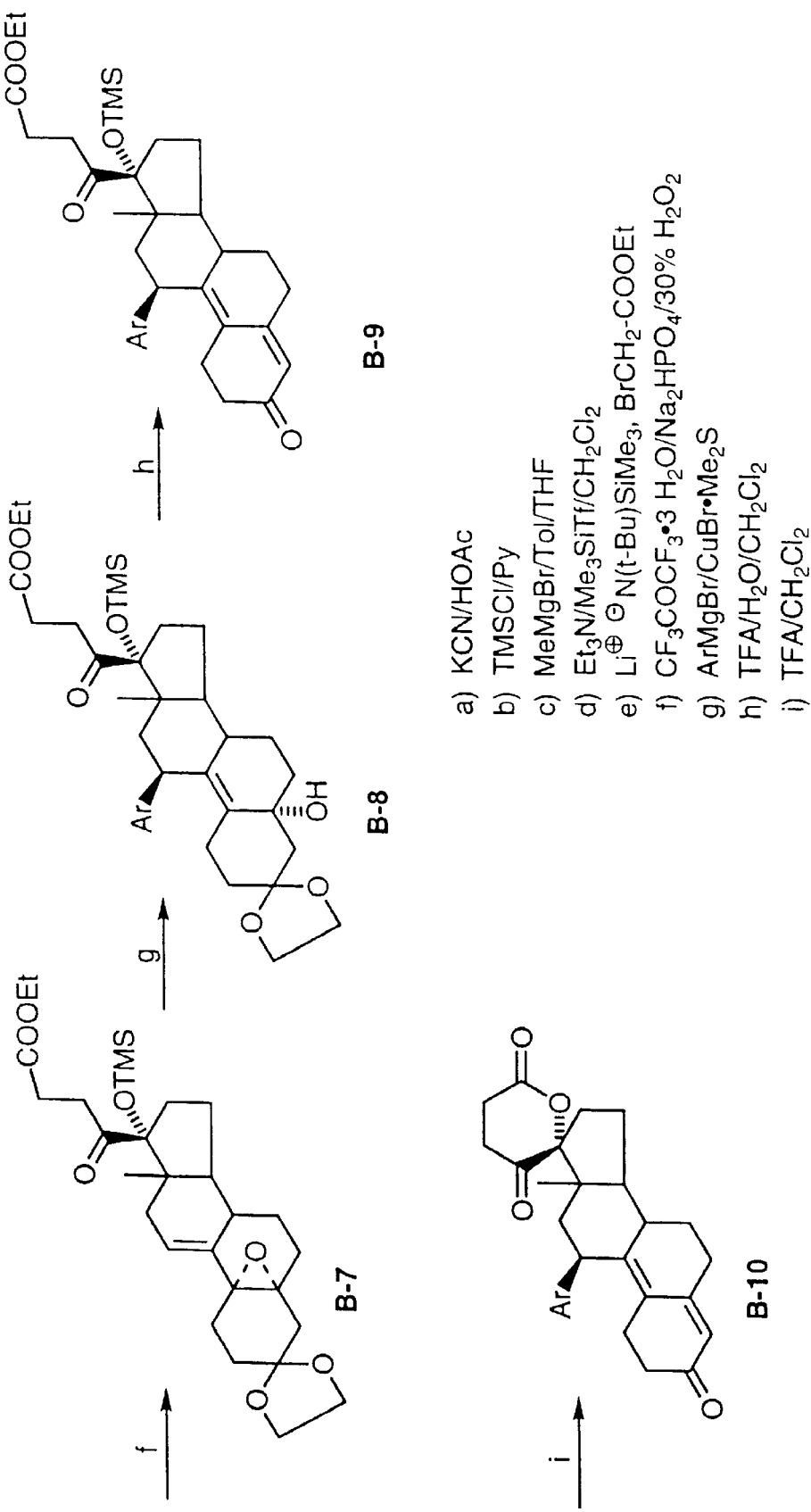

Chart C - 17α-Ethynyl and 17α-Oxymethyl Compounds

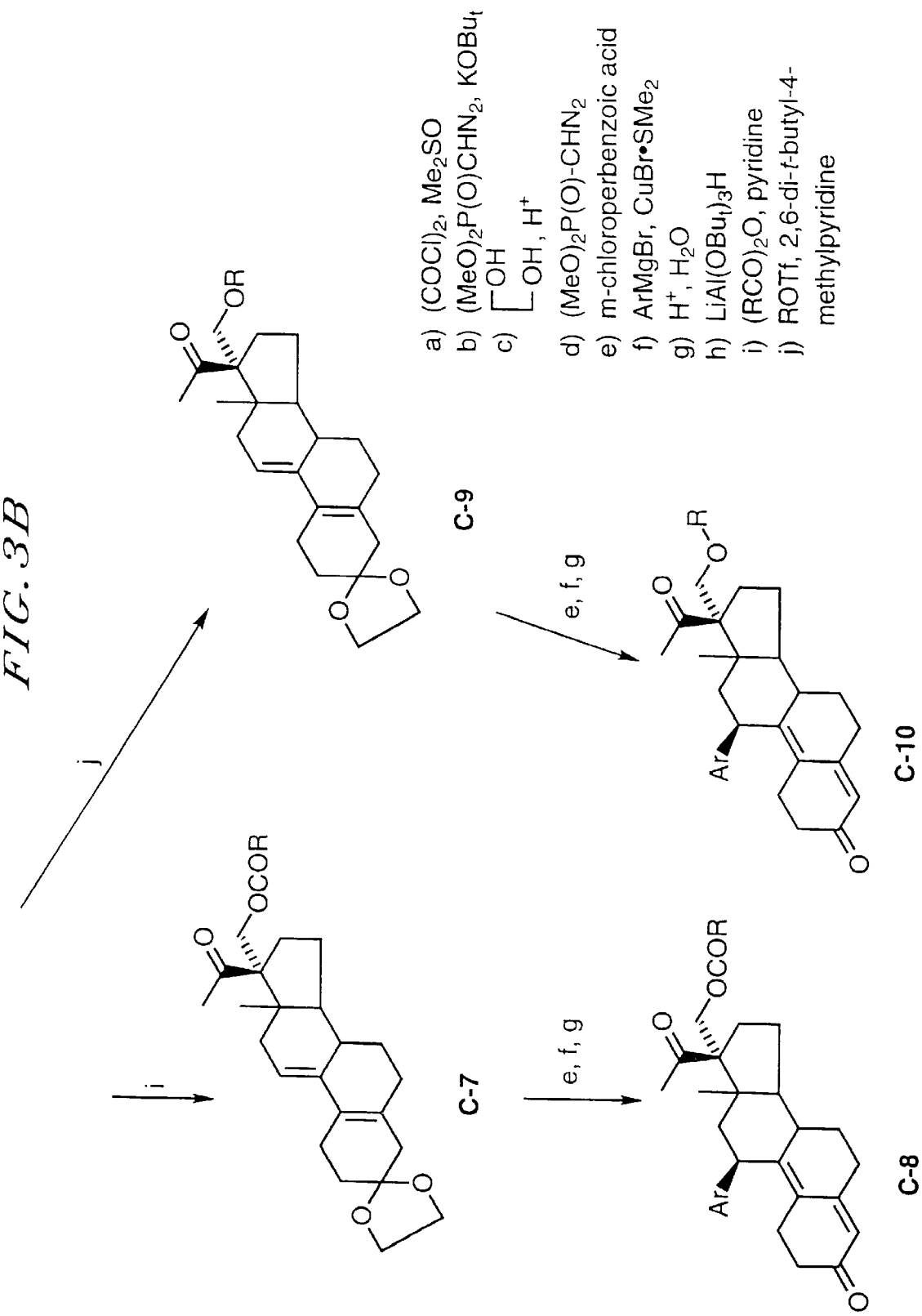

Chart D - Synthesis of 17α-Acyloxy Compounds

Chart E - Synthesis of 17α-Alkyl Compounds a) (EtO)$_2$P(O)-CN, LiCN; SmI$_2$
b) Et$_2$NLi; RX
c) Diisobutylaluminum hydride
d) MeLi
e) pyridinium dichromate
f) H$_2$O$_2$, Na$_2$HPO$_4$, (CF$_3$)$_2$CO
g) ArMgBr, CuBr•SMe$_2$
h) H$^+$, H$_2$O

20-KETO-11β-ARYLSTEROIDS AND THEIR DERIVATIVES HAVING AGONIST OR ANTAGONIST HORMONAL PROPERTIES

BACKGROUND OF THE INVENTION

1. Field of the Invention

This invention relates to a novel class of steroids which are believed to bind to the progestin receptor and which exhibit potent antiprogestational activity, steroid intermediates which are useful for preparing same and methods for the preparation of steroid intermediates. Such compounds are useful for treatment of fibroids, endometriosis, and certain tumors, in causing cervical ripening prior to delivery, in hormone replacement therapy and in control of fertility and reproduction.

2. Discussion of the Background

Progesterone plays a major role in reproductive health and functioning. Its effects on, for example, the uterus, breast, cervix and hypothalamic-pituitary unit are well established. It also has extra-reproductive activities that are less well studied, such as effects on the brain, the immune system, the vascular endothelial system and on lipid metabolism. Given this wide array of effects, it is apparent that compounds which mimic some of the effects of progesterone (agonists), antagonize these effects (antagonists) or exhibit mixed effects (partial agonists or mixed agonist/antagonist) can be useful in treating a variety of disease states and conditions.

Steroid hormones exert their effects, in-part, by binding to intracellular receptors. Compounds that bind to the appropriate receptors and are antagonists or partial agonists of the estrogenic and androgenic hormones have long been known, but it was not until around 1982 that the discovery of compounds that bind to the progesterone receptor and antagonize the effects of progesterone was announced. Since then, a number of such compounds have been reported in the scientific and patent literature and their effects in vitro, in animals and in humans have been studied. Although compounds such as estrogens and certain enzyme inhibitors can prevent the physiological effects of endogenous progesterone, in this discussion "antiprogestin" is confined to those compounds that bind to the progestin receptor.

Information indicating that antiprogestins would be effective in a number of medical conditions is now available. This information has been summarized in a report from the Institute of Medicine (Donaldson, Molly S.; Dorflinger, L.; Brown, Sarah S.; Benet, Leslie Z., Editors, *Clinical Applications of Mifepristone (RU 486) and Other Antiprogestins, Committee on Antiprogestins: Assessing the Science, Institute of Medicine, National Academy Press*, 1993). In view of the pivotal role that progesterone plays in reproduction, it is not surprising that antiprogestins could play a part in fertility control, including contraception (long-term and emergency or post-coital), menses induction and medical termination of pregnancy, but there are many other potential uses that have been supported by small clinical or preclinical studies. Among these are the following:

1. Labor and delivery—antiprogestins may be used for cervical ripening prior to labor induction such as at term or when labor must be induced due to fetal death. They may also be used to help induce labor in term or post-term pregnancies.

2. Treatment of uterine leiomyomas (fibroids)—these non-malignant tumors may affect up to 20% of women over 30 years old and are one of the most common reasons for surgery in women during their reproductive years. Hysterectomy, the common treatment for persistent symptoms, of course results in sterility.

3. Treatment of endometriosis—this common (5 to 15% incidence, much larger in infertile women) and often painful condition is now treated with drugs such as danazol or gonadotrophin-releasing hormone analogs that have significant side-effects, or must be dealt with surgically.

4. Hormone replacement therapy, where they may be given to interupt or curtail the activity of progestins.

5. Cancers, particularly breast cancers - the presence of progestin receptors in many breast cancers has suggested the use of antiprogestins in treating metatstatic cancer or in prevention of recurrence or initial development of cancer.

6. Other tumors such as meningiomas—these brain membrane tumors, although non-malignant, result in death of the patient and nonsurgical treatments are lacking.

7. Male contraception—antiprogestins can interfere with sperm viability, although whether this is an antiprogestational effect or not is controversial, as it may relate to the antiglucocorticoid activity of such compounds.

8. Antiestrogenic effects—at least some antiprogestins oppose the action of estrogens in certain tests, but apparently through a mechanism that does not involve classical hormone receptors. This opens a variety of possibilities for their medical use.

9. Antiglucocorticoid effects—this is a common side-effect of antiprogestins, which can be useful in some instances, such as the treatment of Cushing's syndrome, and could play a role in immune disorders, for example. In other instances it is desirable to minimize such effects.

The effects and uses of progesterone agonists have been well documented. In addition, it has been recently shown that certain compounds structurally related to the known antiprogestins have strong agonist activity in certain biological systems (e.g., the classical progestin effects in the estrogen-primed immature rabbit uterus; cf. C. E. Cook et al., Life Sciences, 52, 155–162 (1993)). Such compounds are partial agonists in human cell-derived receptor systems, where they bind to a site distinct from both the progestin and antiprogestin sites (Wagner et al., Proc. Natl. Acad. Sci., 93, 8739–8744 (1996)). Thus the general class of antiprogestins can have many subclasses, which may vary in their clinical profiles.

The earliest antiprogestins, in addition to having an 11β-aryl substituent, were substituted with a 17β-hydroxyl group and various 17α-substituents. (See for example, Teutsch, Jean G.; Costerousse, Germain; Philibert, Daniel, and Deraedt, Roger. Novel steroids. U.S. Pat. No. 4,386,085. 1983; Philibert, Daniel; Teutsch, Jean G.; Costerousse, Germain, and Deraedt, Roger. 3-Keto-19-nor-Δ-4,9-steroids. U.S. Pat. No. 4,477,445. 1983; Teutsch, Jean G.; Pantin, Germain; Costerousse, Saint-Maurice; Daniel Philibert; La Varenne Saint Hilaire; Roger Deraedt, inventors. Steroid derivatives. Roussel Uclaf, assignee. U.S. Pat. No. 4,447,424. 1984; Cook, C. Edgar; Tallent, C. Ray; Reel, Jerry R., and Wani, Mansukh C. 17α-(Substituted-methyl)-17β-hydroxy/esterified hydroxy steroids and pharmaceutical compositions containing them. U.S. Pat. Nos. 4,774,236 (1988) and 4,861,763 (1989)). Then it was discovered that a 17β-acetyl, 17α-acyloxy group in the presence of 11β-aryl could also generate compounds with antiprogestational effects (Cook, C. Edgar; Lee, Y.-W.; Reel, Jerry R.; Wani, Mansukh C., Rector, Douglas. 11β-Substituted Progesterone Analogs. U.S. Pat. Nos. 4,954,490 (1990) and 5,073,548 (1991)), and various permutations of these findings have been made as well. However, introduction of a 16α-ethyl group or a hydrogen substituent at the 17α-position in the 17β-acyl series of compounds is reported to lead to agonist or partial agonist activity (C. E. Cook et al., Life Sciences, 52, 155–162 (1993)).

Generally, however, antiprogestational activity has always been associated with the presence of an 11β-aryl substituent on the steroid nucleus, together with a $\Delta^{4,9}$-3-ketone or $\Delta^4$-3-ketone moiety. A wide latitude has been reported in the substituents on the 11β-aryl moiety associated with antiprogestational activity (cf. Teutsch, G. and Philibert, D. History and perspectives of antiprogestins from the chemist's point of view. Human Reproduction. Jun; 9(Supplement 1):12–31 (1994)). One novel feature of the present invention is the discovery that to achieve a strong and essentially complete antiprogestational response and little or no agonist effect in a classical in vivo measure of progestational response (the McGinty adaptation of the Clauberg test in the estrogen-primed immature female rabbit), the aromatic group at the 11β-position, in the presence of a 17β-acyl-17α-acyloxy substitution pattern, is best substituted with a basic nitrogen moiety.

The patents of Cook et al. (1989, 1991) referred to above show the use of an acyclic N,N-dimethylamino substituent on the 4-position (para-position) of the 11β-aryl substituent in the presence of the 17β-acetyl, 17α-acyloxy substitution pattern. Ashby et al. (Ashby J; Paton D; Lefevre P A, Cyclic amines as less mutagenic replacements for dimethyl amino (—NMe$_2$) substituents on aromatic organic compounds: implications for carcinogenicity and toxicity. Cancer Lett, 1983 17: 263–71 (1983)) find that use of a cyclic amino substituent on certain carcinogenic aryl compounds markedly reduces or eliminates mutagenicity.

Wunerwald et al. DD 290 198 (1991) entitled in part, "11β-aryl substituierten Estra-4,9-dien-3-one-17 (S)-spiro-1'cyclohexan-2'-onen and 11β-arylsubstituierten Estra-4,9-dien-3-one-17 (S)-spiro-1'cyclohexan-2'-olen sowie deren derivate" illustrates steroid compounds bearing C$_{17}$ spirocyclic ketone and alcohol substitution.

Rohde et al. U.S. Pat. No. 4,609,651 report 11β-Arylestradienes, their production and pharmaceutical preparations containing same. These compounds are 17β-hydroxy- 17α-alkenyl substituted.

Kim et al. PCT WO96/30390 (1996) report a method for preparing 17α-acetoxy-11β-(4-N,N-dimethylaminophenyl)-19-norpregna-4,9-diene-3,20-dione, intermediates useful in the method and method for the preparation of such intermediates. Both the 11β-4-N,N-dimethylaminophenyl and the α-acetoxy groups are indicated as essential. Neither nitrogen heterocycles nor 17α-carbonyloxy groups are suggested.

Kim et al. PCT WO97/4145 reports 21-substituted progesterone derivatives bearing a 11β-substituted phenyl group but no heterocyclic substitutions.

In spite of the clinical promise of antiprogestins, as of Jan. 1, 1998, there were no antiprogestin drugs marketed in the United States or many other countries. Only one antiprogestin drug is approved and available for clinical use anywhere in the world and that drug, mifepristone, is mainly used for medical termination of pregnancy. A number of factors are the cause of this situation, but certainly a need exists for new antiprogestational drugs that can be used for the conditions described above.

Accordingly there remains a need for antiprogestin compounds which exhibit higher specificity.

SUMMARY OF THE INVENTION

Therefore the present invention is directed to cyclic amine substituents such as N-piperidinyl which are particularly beneficial when substituted in the 4-position of the 11β-aryl moiety, since in addition to having the potential for reduction of toxicity we have discovered that they retain not only the gross molecular properties of the dimethylamino analogs, but in addition they exhibit strong binding to the progestin receptor and have potent progestational or antiprogestational activity. Furthermore they exhibit nonclassical antiestrogenic activity.

Another novel feature of the present invention is that cyclization of the amine-containing residue back onto the aromatic ring to form a fused bicyclic system, such as the N-methylindol-5-yl compound, is particularly beneficial in that the resulting compounds have greatly diminished antiglucocorticoid activity.

The 17β-acyl-17α-acyloxy steroids having an 11β-aryl group are characterized by considerable conformational and rotational flexibility that may facilitate their ability to adapt to the binding site and thereby to bind to the progestin receptor in such a manner as to promote antiprogestational activity.

In another novel feature of the present invention, it is found that conversion of these moieties to a 17,17-spiro ring while retaining the 20-ketone and the 17α-O—C(=O) pattern, as in structure II below, results in a much more rigid structure for these moieties nevertheless leads to compounds with potent antiprogestational activity unaccompanied by any significant agonist activity in the McGinty variation of the classical Clauberg assay. Furthermore these compounds surprisingly exhibit markedly reduced binding to the androgen hormone receptor, in contrast to the usual relatively strong androgen receptor binding observed with the known antiprogestins.

A further novel feature of the present invention is that in the presence of the 17β-acyl and 11β-aryl substituents the 17α-O—(C=O)— pattern may be reversed to 17α-C(=O)—O— while retaining strong antiprogestational activity unaccompanied by any significant agonist activity in the McGinty variation of the classical Clauberg assay.

Another embodiment of the present invention is directed to intermediates for the preparation of steroid compounds having progesterone activity which features a C$_5$ hydroxyl group, and method for preparing such compounds by opening of the corresponding C$_{5-10}$ epoxide.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1A:
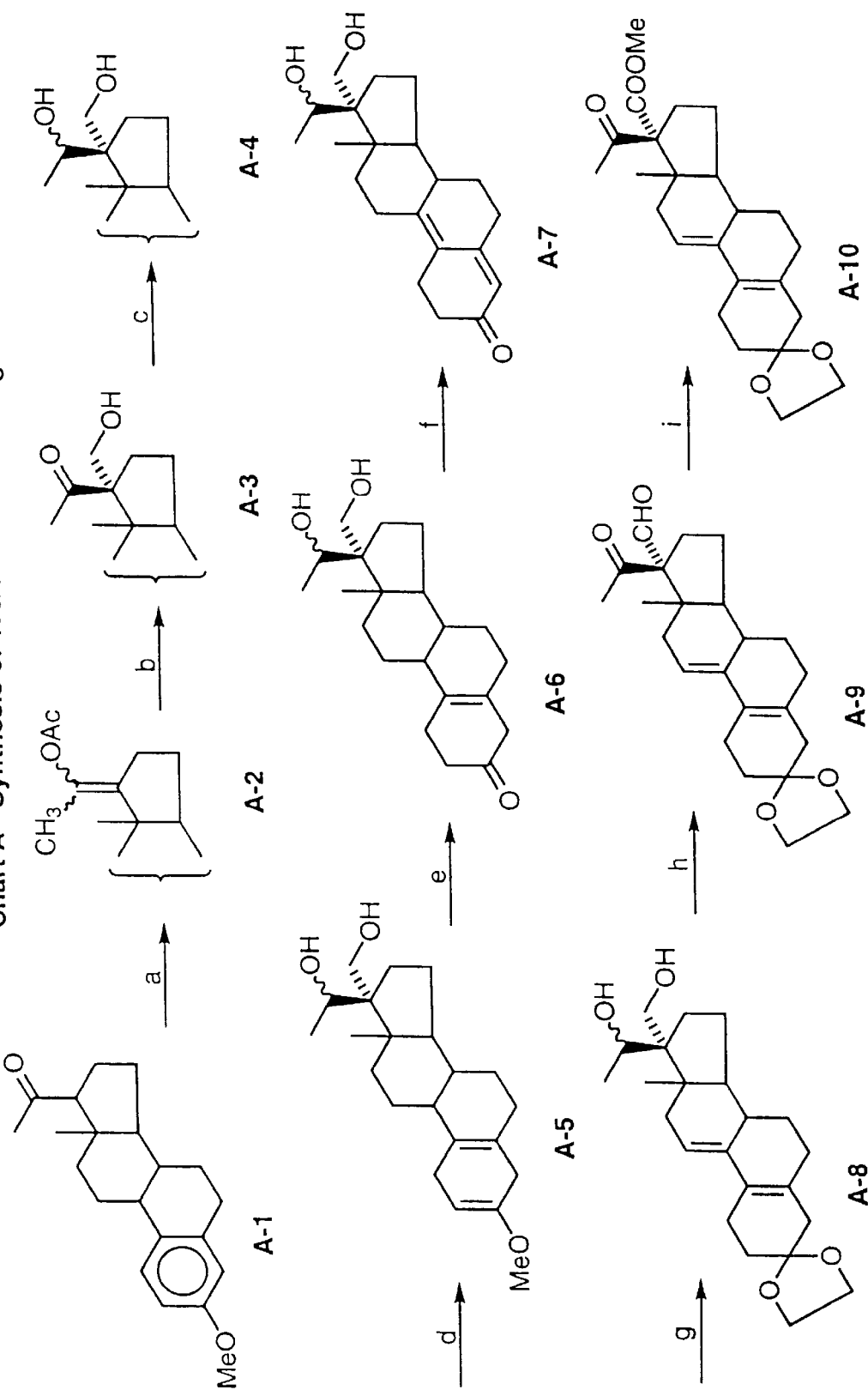
FIG. 1 illustrates a synthetic scheme for preparing 17β-acetyl, 17α-carboxylic ester substituted compounds.

The present invention is directed to a hormonal or antihormonal steroid compound of structure I,

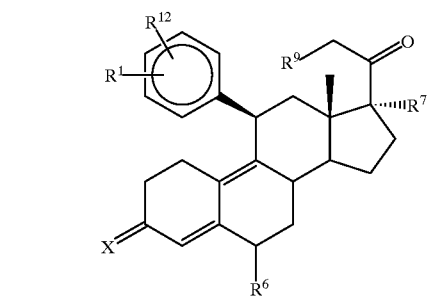
(I)

wherein

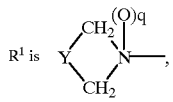

$R^1$ is where q is 0 or 1, Y is —$(CH_2)_m$— where m is an integer of 0 to 5, or Y is —$(CH_2)_n$—Z—$(CH_2)_p$— where n=0 through 2, p =0 through 2 and Z is a heteroatom (optionally substituted and where the $CH_2$ groups may be optionally substituted); or $R^1$ is (N-imidazolyl)- or (N-pyrrolyl)-; and
$R^{12}$ is H or halo; or
$R^1$ and $R^{12}$ combine to form a ring

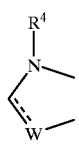

where W is $CH_2$, CH, NH, N, O, or S, and $R^4$ is H, $CH_3$, or $C_2H_5$,

X is O or $NOR^5$, where $R^5$ is H or $C_1$–$C_4$ alkyl, $C_3$–$C_6$ cycloalkyl, $C_2$–$C_4$ alkenyl, $C_2$–$C_4$ alkynyl, $C_6$ aryl, or heteroaryl, any of which may be optionally substituted; or X is (H, H), (H, OH), (H, OSi(lower alkyl)$_3$), or (H, $OCOR^5$), where $R^5$ is $C_1$–$C_4$ alkyl, $C_3$–$C_6$ cycloalkyl, $C_2$–$C_4$ alkenyl, $C_2$–$C_4$alkynyl, $C_6$–$C_2$ aryl, aralkyl, aralkenyl, aralkynyl, heteroaryl, heteroaralkyl, heteroaralkenyl or heteroaralkynyl, any of which may be optionally substituted; or

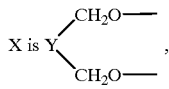

where Y is —$(CH_2)_m$— where m=0 through 3, or Y is —$(CH_2)_n$—Z— $(CH_2)_p$— where n=0 through 2, p=0 through 2 and Z is a heteroatom (optionally substituted) or Z is a carbon atom substituted with one or two lower alkyl groups;

$R^6$ is H, $CH_3$, or halogen;
$R^7$ is H, $C_1$–$C_4$ alkyl, $C_2$–$C_4$ alkenyl, or $C_2$–$C_4$ alkynyl, any of which may be optionally substituted; or $R^7$ is O—CO—$R^8$ or O—$R^8$ where $R^8$ is H, $C_1$–$C_{18}$ alkyl, $C_2$–$C_{18}$ alkenyl, $C_2$–$C_{18}$ alkynyl, $C_4$–$C_8$ cycloalkyl, $C_6$–$C_{12}$ aryl, aralkyl, aralkenyl, aralkynyl, heteroaryl, heteroaralkyl, heteroaralkenyl or heteroaralkynyl, any of which may be optionally substituted; and $R^9$ is H, lower alkyl, alkenyl or alkynyl, halo, O—CO—$R^8$ or $OR^8$ where $R^8$ is as defined above, and pharmaceutically acceptable salts thereof.

In a preferred embodiment, the group $R^1$ or the nitrogen atom of the ring formed by $R^1$ and $R^{12}$ is in the 4- position of the phenyl ring.

According to another embodiment of the present invention is a hormonal or antihormonal steroid compound of structure II,

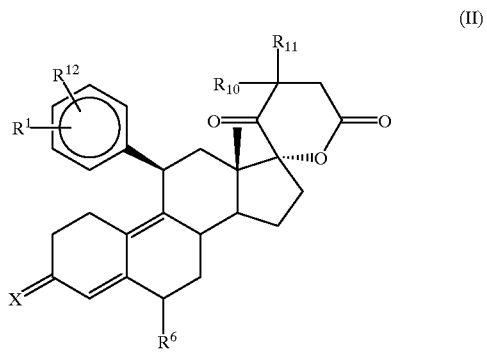
(II)

wherein $R^1$ is ($R^2R^3$N)—, where $R^2$ and $R^3$ may be combinations of H, $C_1$–$C_4$ alkyl, $C_3$–$C_6$ cycloalkyl, $C_2$–$C_4$ alkenyl or $C_2$–$C_4$ alkynyl, any of which may be optionally substituted; or $R^1$ is ($R^2R^3$N(O))—, where $R^2$ and $R^3$ may be combinations of $C_1$–$C_4$ alkyl, $C_3$–$C_6$ cycloalkyl, $C_2$–$C_4$ alkenyl or $C_2$–$C_4$ alkynyl, any of which may be optionally substituted; or wherein

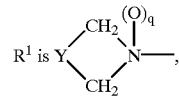

$R^1$ is where q is 0 or 1, Y is —$(CH_2)_m$— where m is an integer of 0 to 5, or Y is —$(CH_2)_n$—Z—$(CH_2)_p$— where n=0 through 2, p=0 through 2, and Z is a heteroatom (optionally substituted and where the $CH_2$ groups may be optionally substituted); or $R^1$ is (N-imidazolyl)- or (N-pyrrolyl)-; or
$R^1$ is halo-, HO—, $CF_3SO_2O$—, $CH_3O$—, $CH_3S$—, $CH_3S(O)$—, $CH_3S(O_2)$—, $CH_3CO$—, $CH_3CH(OH)$—, NC—, HCC—, $C_6H_5CC$—, (2'-or 3'-furyl)-, (2'- or 3'-thiophenyl)-, (2'-, 3'- or 4'-pyridyl)-, (2'-thiazolyl)-, (2'-N-methylimidazolyl)-, (5'-pyrimidinyl)-, $C_6H_5$—, HCC—, $H_2C$=CH—, $C_2H_5$—, or MeC(=$CH_2$)—; and $R^{12}$ is H or halo; or
$R^1$ and $R^{12}$ combine to form a ring

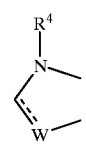

where W is $CH_2$, CH, NH, N, O, or S, and $R^4$ is H, $CH_3$, or $C_2H_5$;

X is O or $NOR^5$, where $R^5$ is H or $C_1$–$C_4$ alkyl, $C_3$–$C_6$ cycloalkyl, $C_2$–$C_4$ alkenyl, $C_2$–$C_4$ alkynyl, $C_6$ aryl, or heteroaryl, any of which may be optionally substituted; or X is (H, H), (H, OH), (H, OSi(lower alkyl)$_3$), or (H, $OCOR^5$), where $R^5$ is $C_1$–$C_4$ alkyl, $C_3$–$C_6$ cycloalkyl, $C_2$–$C_4$ alkenyl, $C_2$–$C_4$alkynyl, $C_6$–$C_{12}$ aryl, aralkyl, aralkenyl, aralkynyl, heteroaryl, heteroaralkyl, heteroaralkenyl or heteroaralkynyl, any of which may be optionally substituted; or

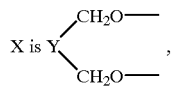

where Y is —$(CH_2)_m$— where m=0 through 3, or Y is —$(CH_2)_m$—Z—$(CH_2)_p$— where n=0 through 2, p=0 through 2 and Z is a heteroatom (optionally substituted) or Z is a carbon atom substituted with one or two lower alkyl groups;

$R^6$ is H, $CH_3$, or halogen;

$R^{10}$ and $R^{11}$ are H, $C_1$–$C_4$ alkyl, $C_2$–$C_4$ alkenyl, $C_2$–$C_4$ alkynyl, $C_4$–$C_8$ cycloalkyl, $C_6$ aryl, aralkyl, aralkenyl, aralkynyl, heteroaralkyl, heteroaralkenyl or heteroaralkynyl, any of which may be optionally substituted, or $R^{10}$ and $R^{11}$ form with the attached carbon atom an optionally substituted $C_3$–$C_8$ cycloalkyl structure and pharmaceutically acceptable salts thereof.

In a preferred embodiment, the group $R^1$ or the nitrogen atom of the ring formed by $R^1$ and $R^{12}$ is in the 4-position of the phenyl ring.

According to another embodiment of the present invention is a hormonal or antihormonal steroid compound of structure I,

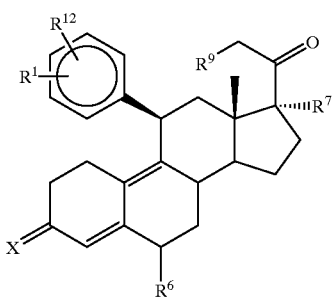

(I)

wherein $R^1$ is $(R^2R^3N)$—, where $R^2$ and $R^3$ may be combinations of H, $C_1$–$C_4$ alkyl, $C_3$–$C_6$ cycloalkyl, $C_2$–$C_4$ alkenyl or $C_2$–$C_4$ alkynyl, any of which may be optionally substituted; or $R^1$ is $(R^2R^3N(O))$—, where $R^2$ and $R^3$ may be combinations of $C_1$–$C_4$ alkyl, $C_3$–$C_6$ cycloalkyl, $C_2$–$C_4$ alkenyl or $C_2$–$C_4$ alkynyl, any of which may be optionally substituted; or wherein

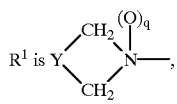

where q is 1 or 1, Y is —$(CH_2)_m$— where m is an integer of 0 to 5, or Y is —$(CH_2)_n$—Z—$(CH_2)_p$— where n=0 through 2, p=0 through 2, and Z is a heteroatom (optionally substituted and where the $CH_2$ groups may be optionally substituted); or $R^1$ is (N-imidazolyl)- or (N-pyrrolyl)-; and $R^{12}$ is H or halogen ;or $R^1$ and $R^{12}$ combine to form a ring

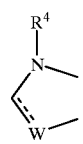

where W is $CH_2$, CH, NH, N, O, or S, and $R^4$ is H, $CH_3$, or $C_2H_5$; or $R^1$ is halo-, HO—, $CF_3SO_2O$—, $CH_3O$—, $CH_3S$—, $CH_3S(O)$—, $CH_3S(O_2)$—, $CH_3CO$—, $CH_3CH(OH)$—, NC—, HCC—, $C_6H_5CC$—, (2'-or 3'-furyl)-, (2'- or 3'-thiophenyl)-, (2'-, 3'- or 4'-pyridyl)-, (2'-thiazolyl)-, (2'-N-methylimidazolyl)-, (5'-pyrimidinyl)-, $C_6H_5$—, HCC—, $H_2C$=CH—, $C_2H_5$—, or MeC(=$CH_2$)—;

X is O or $NOR^5$, where $R^5$ is H or $C_1$–$C_4$ alkyl, $C_3$–$C_6$ cycloalkyl, $C_2$–$C_4$ alkenyl, $C_2$–$C_4$ alkynyl, $C_6$ aryl, or heteroaryl, any of which may be optionally substituted; or X is (H, H), (H, OH), (H, OSi(lower alkyl)$_3$), or (H ,$OCOR^5$), where $R^5$ is $C_1$–$C_4$ alkyl, $C_3$–$C_6$ cycloalkyl, $C_2$–$C_4$ alkenyl, $C_2$–$C_4$ alkynyl, $C_6$–$C_{12}$ aryl, aralkyl, aralkenyl, aralkynyl, heteroaryl, heteroaralkyl, heteroaralkenyl or heteroaralkynyl, any of which may be optionally substituted; or X is

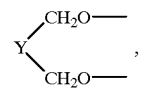

where Y is —$(CH_2)_m$— where m=0 through 3, or Y is —$(CH_2)_n$—Z— $(CH_2)_p$— where n=0 through 2, p=0 through 2 and Z is a heteroatom (optionally substituted) or Z is a carbon atom substituted with one or two lower alkyl groups;

$R^6$ is H, $CH_3$, or halogen;

$R^7$ is $COOR^8$ or O—$R^8$ where $R^8$ is H, $C_1$–$C_{18}$ alkyl, $C_2$–$C_{18}$ alkenyl, $C_2$–$C_{18}$ alkynyl, $C_4$–$C_8$ cycloalkyl, $C_6$–$C_{12}$ aryl, aralkyl, aralkenyl, aralkynyl, heteroaryl, heteroaralkyl, heteroaralkenyl or heteroaralkynyl, any of which may be optionally substituted; and $R^9$ is H, lower alkyl, alkenyl or alkynyl, halo or O—CO—$R^8$, where $R^8$ is as defined above, or O—$R^8$ where $R^8$ is as defined above and pharmaceutically acceptable salts thereof In a preferred embodiment, the group $R^1$ or the nitrogen atom of the ring formed by $R^1$ and $R^{12}$ is in the 4- position of the phenyl ring.

In another embodiment of the present invention is an intermediate for the preparation of a hormonal or antihormonal steroid compound, of the formula (III)

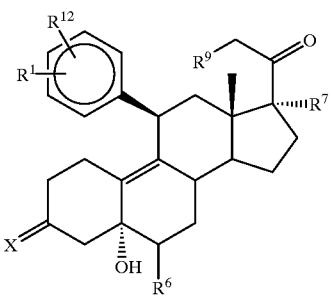

(III)

wherein $R^1$ is $(R^2R^3N)$—, where $R^2$ and $R^3$ may be combinations of H, $C_1$–$C_4$ alkyl, $C_3$–$C_6$ cycloalkyl, $C_2$–$C_4$ alkenyl or $C_2$–$C_4$ alkynyl, any of which may be optionally substituted; or $R^1$ is $(R^2R^3N(O))$—, where $R^2$ and $R^3$ may be combinations of $C_1$–$C_4$ alkyl, $C_3$–$C_6$ cycloalkyl, $C_2$–$C_4$ alkenyl or $C_2$–$C_4$ alkynyl, any of which may be optionally substituted; or wherein

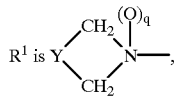

where q is 0 or 1, Y is —$(CH_2)_m$— where m is an integer of 0 to 5, or Y is —$(CH_2)_n$—Z—$(CH_2)_p$— where n=0 through 2, p=0 through 2 and Z is a heteroatom (optionally substituted and where the $CH_2$ groups may be optionally substituted); or $R^1$ is (N-imidazolyl)- or (N-pyrrolyl)-; or $R^1$ is halo-, HO—, $CF_3SO_2O$—, $CH_3O$—, $CH_3S$—, $CH_3S(O)$—, $CH_3S(O_2)$—, $CH_3CO$—, $CH_3CH(OH)$—, NC—, HCC—, $C_6H_5CC$—, (2'- or 3'-furyl)-, (2'- or 3'-thiophenyl)-, (2'-, 3'- or 4'-pyridyl)-, (2'-thiazolyl)-, (2'-N-methylimidazolyl)-, (5'-pyrimidinyl)-, $C_6H_5$—, HCC—, $H_2C=CH$—, $C_2H_5$—, or $MeC(=CH_2)$—; and $R^{12}$ is H or halo; or $R^1$ and $R^{12}$ combine to form a ring

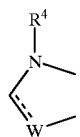

where W is $CH_2$, CH, NH, N, O, or S, and $R^4$ is H, $CH_3$, or $C_2H_5$;

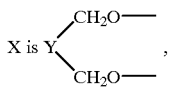

where Y is —$(CH_2)_m$— where m=0 through 3, or Y is —$(CH_2)_n$—Z—$(CH_2)_p$— where n=0 through 2, p=0 through 2 and Z is a heteroatom (optionally substituted) or Z is a carbon atom substituted with one or two lower alkyl groups;

$R^6$ is H, $CH_3$, or halogen;

$R^7$ is H, $C_1$–$C_4$ alkyl, $C_2$–$C_4$ alkenyl, or $C_2$–$C_4$ alkynyl, any of which may be optionally substituted; O—CO—$R^8$, $COOR^8$, or O—$R^8$ where $R^8$ is H, $C_1$–$C_{18}$ alkyl, $C_2$–$C_{18}$ alkenyl, $C_2$–$C_{18}$ alkynyl, $C_4$–$C_8$ cycloalkyl, $C_6$–$C_{12}$ aryl, aralkyl, aralkenyl, aralkynyl, heteroaryl, heteroaralkyl, heteroaralkenyl or heteroaralkynyl, any of which may be optionally substituted; and $R^9$ is H, lower alkyl, alkenyl or alkynyl, halo, O—CO—$R^8$ or O—$R^8$ where $R^8$ is as defined above, and pharmaceutically acceptable salts thereof.

In a preferred embodiment, the group $R^1$ or the nitrogen atom of the ring formed by $R^1$ and $R^{12}$ is in the 4-position of the phenyl ring.

The above-identified compounds of formula I and II specifically include compounds which are subsituted on the A ring at the 3-position with two hydrogen atoms. These compounds are believed to undergo oxidation in vivo to the corresponding carbonyl compound.

Within the scope of the present invention, the term heteroatom means oxygen, nitrogen, sulfur, silicon or boron. Halogen means fluorine, chlorine, bromine or iodine and halo means fluoro, chloro, bromo or iodo. Aralkyl, aralkenyl, or aralkynyl means a $C_1$–$C_4$ alkyl, $C_2$–$C_4$ alkenyl or $C_2$–$C_4$ alkynyl group bearing an aryl substituent. Lower alkyl means a $C_1$–$C_4$ alkyl group. Heteroaryl means a unit of 5 to 12 non-hydrogen atoms consisting of one or more cyclic structures that may be fused or linked together, which contain 1 to 5 heteroatoms and which are generally accepted by those skilled in the art as having aromatic electronic character.

Heteroaralkyl, heteroaralkenyl, or heteroaralkynyl means a $C_1$–$C_4$ alkyl, $C_2$–$C_4$ alkenyl or $C_2$–$C_4$ alkynyl group bearing a heteroaryl substituent.

"Optionally substituted" means unsubstituted or substituted with one or more heteroatom(s) and/or halogens and/or alkyl groups of 1 to 4 carbon atoms and/or alkenyl and/or alkynyl groups of 2 to 4 carbon atoms and/or cycloalkyl groups of 3 to 7 carbon atoms and/or aryl groups of 6 to 12 carbon atoms and/or heteroaryl groups, and in which the alkyl, alkenyl, alkynyl, cycloalkyl, aryl or heteroaryl group may be further substituted with one or more heteroatoms and/or halogens. Substitution may occur directly on $CH_2$ groups of cyclic amine heterocycles. Where their valency permits, heteroatoms may be substituted either within the carbon chain or by attachment to it by single or double bonds. For example, —$CH_2$— $CH_2$—CH=O, —$CH_2$(C=O)—$CH_3$, —$CH_2$—$CH_2$—O—$CH_3$, —$CH_2$—$CH_2$—$CH_2OH$, $CH_3$—$CH_2$—$CH_2O$—, $CH_2$— $CH_2$—C(=O)—$NH_2$, $CH_3$—$CH_2$—C(O)—NH— and $CF_3$—CC— all fall within this definition.

In all cases where valency and steric considerations permit, alkyl, alkenyl, alkynyl and cycloalkyl groups may contain additional double or triple bonds and/or branched chains.

The group $R^6$ at $C_6$ as it appears in structures I, II and III may be in either the α or β position. In a preferred embodiment, the group $R^6$ is located in the α-position.

In another embodiment, the $C_{11}$β-aryl group may be replaced with a pyridine group substituted with groups $R^1$ and $R^{12}$ as previously described. Specifically, the present invention provides for substitution at the $C_{11}$ position with a dialkylaminopyridyl or cycloaminopyridyl group in all compounds where a dialkylaminophenyl or a cycloaminophenyl group is suggested.

In a preferred embodiment, the steroid having structure I is substitued as follows:

$R^1$—Ph is 4-(N-piperidino)phenyl, 4-(N-pyrrolidino)phenyl, 4-(N-morpholino)phenyl, 1-methylindol-5-yl or 1-methyl-2,3-dihydroindol-5-yl);

X is O, NOH, or NOCH$_3$;

R$^6$ is H, CH$_3$, F or Cl;

R$^7$ is H, methyl, ethyl, ethynyl, 1-propynyl, trifluoro-1-propynyl, 3-hydroxypropyn-1-yl, propyl, 3-hydroxypropyl, 3-hydroxy-1-propenyl (E- or Z-), acetoxy, propionoxy, benzylcarboxy, benzoyloxy or methoxymethyl; and R$^9$ is H, CH$_3$, acetoxy, fluoro, chloro or methoxy In another preferred embodiment, the steroid having structure II is subsituted as follows:

R$^1$—Ph is 4-aminophenyl, 4-(N-methylamino)phenyl, 4-(N,N-dimethylamino)phenyl, 4-(N-piperidino)phenyl, 4-(N-pyrrolidino)phenyl, 4-(N-morpholino)phenyl, 1-methylindol-5-yl, 1-methyl-2,3-dihydroindol-5-yl, 4-methoxyphenyl, 4-acetylphenyl, 4-(methylthio)phenyl or 4-(methylsulfinyl)phenyl;

X is O, NOH, or NOCH$_3$;

R$^6$ is H, CH$_3$, F or Cl;

R$^{10}$R$^{11}$ is H$_2$, (CH$_3$, H), (H, CH$_3$) or (CH$_3$)$_2$.

In another preferred embodiment, the steroid having structure I is substituted as follows:

R$^1$—Ph is 4-aminophenyl, 4-(N-methylamino)phenyl, 4-(N,N-dimethylamino)phenyl, 4-(N-piperidino)phenyl, 4-(N-pyrrolidino)phenyl, 4-(N-morpholino)phenyl, 1-methylindol-5-yl, 1-methyl-2,3-dihydroindol-5-yl, 4-methoxyphenyl, 4-acetylphenyl, 4-(methylthio)phenyl or 4-(methylsulfinyl)phenyl;

X is O, NOH, or NOCH$_3$;

R$^6$ is H, CH$_3$, F or Cl;

R$^7$ is COOR$^8$ where R$^8$ is methyl, ethyl, propyl, phenyl or benzyl; and

R$^9$ is H, CH$_3$, methoxy, acetoxy, fluoro or chloro

Specific non-limiting examples include the compounds 17α-acetoxy-11β-(4-(N-piperidino)phenyl)-19-norpregna-4,9-diene-3,20-dione, 17α-(-acetoxy-11β-(4-(N-pyrrolidino)phenyl)-19-norpregna-4,9-diene-3,20-dione, 17α-acetoxy-11β-(1-methylindol-5-yl)-19-norpregna-4,9-diene-3,20-dione, 17α-acetoxy-11β-(1-methyl-2,3-dihydroindol-5-yl)-19-norpregna-4,9-diene-3,20-dione, 11β-(4-(N-piperidino)phenyl)-17α-propionyloxy-19-norpregna-4,9-diene-3,20-dione, 17α-propionyloxy-11β-(4-(N-pyrrolidino)phenyl)-19-norpregna-4,9-diene-3,20-dione, 11β-(1-methylindol-5-yl)-17α-propionyloxy-19-norpregna-4,9-diene-3,20-dione, 11β-(1-methyl-2,3-dihydroindol-5-yl)-17α-propionyloxy-19-norpregna-4,9-diene-3,20-dione, 11β-(4-(N,N-dimethylamino)phenyl)-3,20-dioxo-17α-hydroxy-19,21-dinorchola-4,9-dien-24-oic acid δ-lactone, 11β-(4-(N-piperidino)phenyl)-3,20-dioxo-17α-hydroxy-19,21-dinorchola-4,9-dien-24-oic acid δ-lactone, 11β-(1-methylindol-5-yl)-3,20-dioxo-17α-hydroxy-19,21-dinorchola-4,9-dien-24-oic acid δ-lactone, 11β-(1-methyl-2,3-dihydroindol-5-yl)-3,20-dioxo-17α-hydroxy-19,21-dinorchola-4,9-dien-24-oic acid δ-lactone, 17α-carbomethoxy-11β-(4-(N,N-dimethylamino)phenyl)-19-norpregna-4,9-diene-3,20-dione, 17α-carbomethoxy-11β-(4-(N-piperidino)phenyl)-19-norpregna-4,9-diene-3,20-dione, 17α-carbomethoxy-11β-(1-methylindol-5-yl)-19-norpregna-4,9-diene-3,20-dione, 17α-carbomethoxy-11β-(1-methyl-2,3-dihydroindol-5-yl)-19-norpregna-4,9-diene-3,20-dione.

Those compounds of the present invention which bear an amino group on the C$_{11}$ phenyl group accordingly may also comprise a salt formed with the amine. Suitable pharmaceutically acceptable salts are known to those of ordinary skill in the art and comprise carboxylates, sulfates, phosphates and halides.

Steroids having progestational, antiprogestational and/or antiglucocorticoid activity have use in the control of fertility in humans and non-human mammals such as primates, domestic pets and farm animals, and in the treatment of medical conditions in animals or humans in which these activities are beneficial. Thus they may be useful in the treatment of conditions such as fibroids, Cushing's syndrome, glaucoma, endometriosis, cervical ripening prior to delivery, hormone replacement therapy, premenstrual syndrome and cancer in addition to their use in the control of fertility and reproduction.

The compounds of the present invention may be administered by a variety of methods. Thus, those products of the invention that are active by the oral route may be administered in solutions, suspensions, emulsions, tablets, including sublingual and intrabuccal tablets, soft gelatin capsules, including solutions used in soft gelatin capsules, aqueous or oil suspensions, emulsions, pills, lozenges, troches, tablets, syrups or elixirs and the like. Products of the invention active on parenteral administration may be administered by depot injection, implants including Silastic™ and biodegradable implants, intramuscular and intravenous injections.

Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame or saccharin.

Ophthalmic formulations, as is known in the art, will be adjusted for osmotic pressure.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the invention suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present.

The pharmaceutical composition of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol. Among the acceptable vehicles and solvents that may be employed are water and Ringer's solution, an isotonic sodium chloride. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Sterilization may be performed by conventional methods known to those of ordinary skill in the art such as by aseptic filtration, irradiation or terminal sterilization (e.g. autoclaving).

Aqueous formulations (i.e oil-in-water emulsions, syrups, elixers and injectable preparations) may be formulated to achieve the pH of optimum stability. The determination of the optimum pH may be performed by conventional methods known to those of ordinary skill in the art. Suitable buffers may also be used to maintain the pH of the formulation.

The compounds of this invention may also be administered in the form of suppositories for rectal administration of the drug. These compositions can be prepared by mixing the drug with a suitable nonirritating excipient which is solid at ordinary temperatures but liquid at the rectal temperatures and will therefore melt in the rectum to release the drug. Non-limiting examples of such materials are cocoa butter and polyethylene glycols.

They may also be administered by intranasal, intraocular, intravaginal, and intrarectal routes including suppositories, insufflation, powders and aerosol formulations.

Products of the invention which are preferably administered by the topical route may be administered as applicator sticks, solutions, suspensions, emulsions, gels, creams, ointments, pastes, jellies, paints, powders, and aerosols.

Products having anti-glucocorticoid activity are of particular value in pathological conditions characterized by excess endogenous glucocorticoid such as Cushing's syndrome, hirsutism and in particular when associated with the adrenogenital syndrome, ocular conditions associated with glucocorticoid excess such as glaucoma, stress symptoms associated with excess glucocorticoid secretion and the like.

Products having progestational activity are of particular value as progestational agents, ovulation inhibitors, menses regulators, contraceptive agents, agents for synchronization of fertile periods in cattle, endometriosis, and the like. When used for contraceptive purposes, they may conveniently be admixed with estrogenic agents, such as for example as ethynylestradiol or estradiol esters.

Products having anti-progestational activity are characterized by antagonizing the effects of progesterone. As such, they are of particular value in control of hormonal irregularities in the menstrual cycle and for synchronization of fertile periods in cattle.

The compounds of the invention may be used for control of fertility during the whole of the reproductive cycle. They are of particular value as postcoital contraceptives, for rendering the uterus inimical to implantation, and as "once a month" contraceptive agents. They may be used in conjunction with prostaglandins, oxytocics and the like.

A further important utility for the products of the invention lies in their ability to slow down growth of hormone-dependent cancers. Such cancers include kidney, breast, endometrial, ovarian cancers, and prostate cancer which are characterized by possessing progesterone receptors and may be expected to respond to the products of this invention. Other utilities of anti-progestational agents include treatment of fibrocystic disease of the breast. Certain cancers and in particular melanomas may respond favorably to corticoid/anticorticoid therapy.

The compounds according to the present invention may be administered to any warm-blooded mammal such as humans, domestic pets, and farm animals. Domestic pets include dogs, cats, etc. Farm animals include cows, horses, pigs, sheep, goats, etc.

The amount of active ingredient that may be combined with a carrier material to produce a single dosage form will vary depending upon the disease treated, the mammalian species, and the particular mode of administration. A therapeutically effective amount may be determined by routine experimentation and by analogy from the amounts used to treat the same disease states with analogous steroid compounds. For example, a unit dose of the steroid may preferably contain between 0.1 milligram and 1 gram of the active ingredient. A more preferred unit dose is between 0.001 and 0.5 grams. For the specific treatment of endometriosis or fibroids an amount of 0.01 to 10 mg/kg of body weight, preferably from 0.3 to 3 mg/kg, more preferably from 0.1 to 1 mg/kg may be administered orally. Similar dosages may be used for the other therapeutic purposes of these compounds. Ordinarily the compounds may be administered daily 1 to 4 times per day, preferably 1 to 2 times per day, but for uses such as for example in hormone replacement therapy, they may be administered in a cyclophasic regimen. In any case the frequency and timing of dosage will depend upon factors such as the half-life of the specific compound in the body, the dosage formulation and the route of administration. It will be understood, however, that the specific dose level for any particular patient will depend on a variety of factors including the activity of the specific compound employed; the age, body weight, general health, sex and diet of the individual being treated the time and route of administration; the rate of excretion: other drugs which have previously been administered; and the severity of the particular disease undergoing therapy, as is well understood by those of skill in the art.

Having generally described this invention, a further understanding can be obtained by reference to certain general examples which are provided herein for purposes of illustration.

Figure 1B:
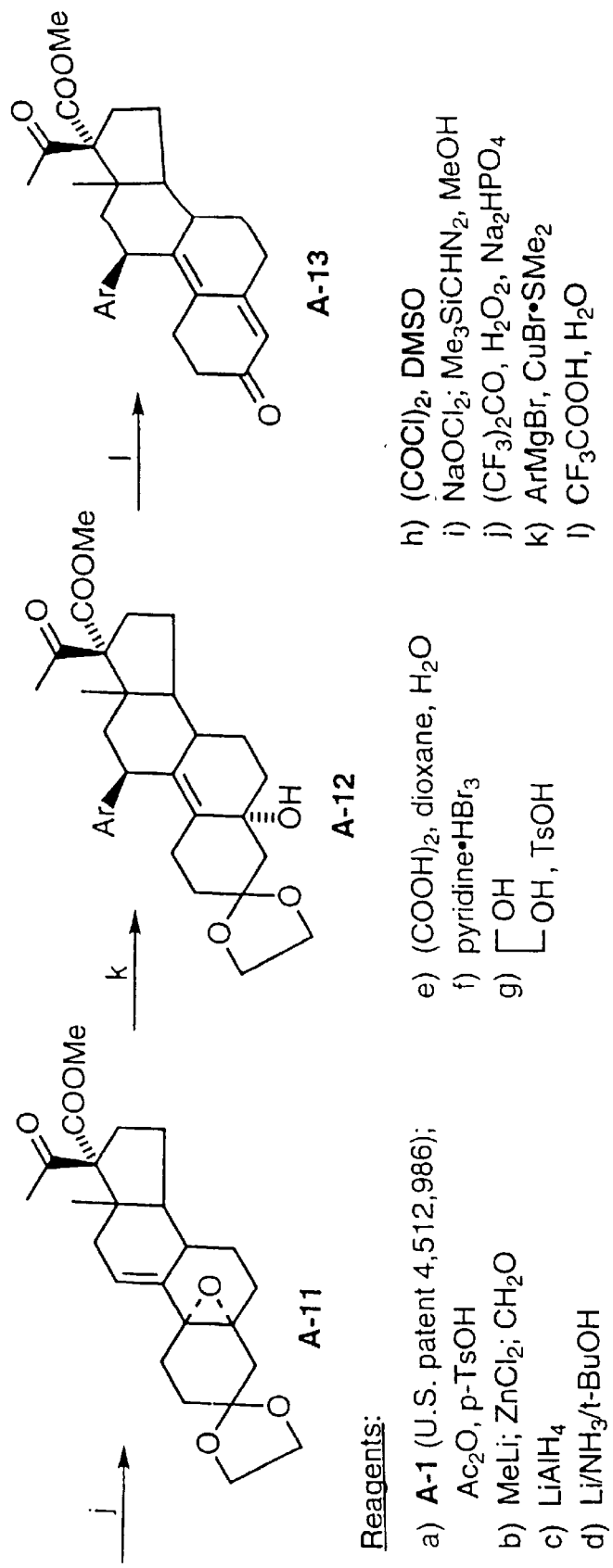

Compounds of this invention may be made by conventional methods known to those of ordinary skill in the art, such as by the procedures outlined in FIGS. 1–5. Thus, for example, as illustrated in FIG. 1, compound A-13 (Ar=4-Me$_2$N—C$_6$H$_4$—) may be made beginning with the known compound 3-methoxy-19-norpregna-1,3,5(10)-trien-20-one (A-1, see U.S. Pat. No. 4,512,986). This is converted to the enol acetate A-2 by treatment with acetic anhydride in the presence of p-toluenesulfonic acid. Reaction of this compound with methyl lithium generates the enolate ion, which in the presence of ZnCl$_2$ reacts with formaldehyde to give the 17α-hydroxy-methyl compound A-3. The 20-ketone may be reduced by a variety of hydride reagents, such as LiAlH$_4$, to A-4, which is generally obtained as a mixture of diol isomers, epimeric at C-20. These need not be separated (although they can be if desired), but can be converted by lithium in ammonia to the dienol ether A-5, which can be hydrolyzed with a mild acid, such as preferably oxalic acid, to the 5(10)-en-3-one A-6. Treatment of A-6 with pyridinium tribromide gives the 4,9-dien-3-one A-7, from which the ketal A-8 may be obtained in the usual manner with ethylene glycol in the presence of an acid such as p-toluenesulfonic acid. Oxidation of both hydroxyl groups to carbonyls can then be carried out with oxalyl chloride/dimethylsulfoxide (Swern reagent) and further oxidation of the resulting A-9 with NaOCl$_2$ converts the 17α-formyl group to a carboxylic acid that reacts with Me$_3$SiCHN$_2$ and methanol to yield the methyl ester A-10. Epoxidation of the 5(10) double bond A-10 with H$_2$O$_2$ in the presence of hexafluoroacetone and Na$_2$HPO$_4$ yields epoxide A-11, which undergoes reaction with arylmagnesium bromides in the presence of Cu(I) salts such as CuBr/dimethylsulfide complex to yield, for example, compound A-12 (Ar= 4Me$_2$N—C$_6$H$_4$—), convertible with acid, preferably hydrochloric acid with methanol, to 17α-carbomethoxy-11β-(4-(N,N-dimethylamino)phenyl)-19-norpregna-4,9-diene-3, 20-dione (A-13, Ar=4—Me$_2$N—C$_6$H$_4$-).

Figure 2A:
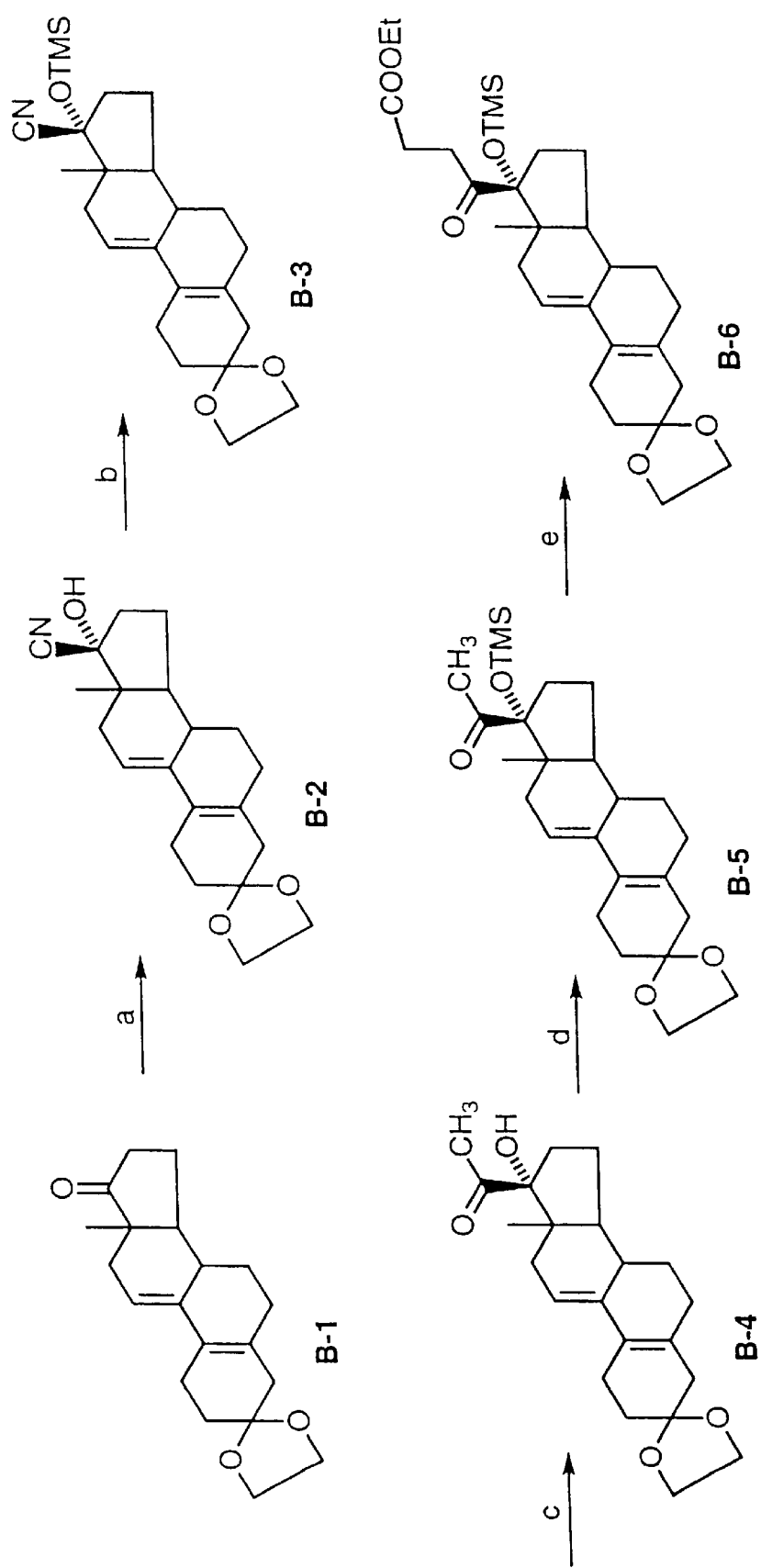
FIG. 2 illustrates a synthetic scheme for preparing 17-spirolactone compounds.

11β-Aryl steroids incorporating a 6-membered 17,17-spirolactone group may be synthesized according to a procedure such as that outlined in FIG. 2. The 17-keto moiety of compound B-I is converted to the 17β-cyano-17α-hydroxy cyanohydrin B-2 with sodium cyanide and acetic acid, and then the hydroxyl group is protected with a trimethylsilyl group in the usual way. Cyano compound B-3 is then converted to the 17α-hydroxy-20-ketone B-4 by reaction with methylmagnesium bromide and the 17α-OH is again protected as its silyl ether. Alkylation of the resulting B-5 by use of a metal amide such as preferably lithium t-butyl trimethylsilylamide and an α-haloester such as ethyl bromoacetate yields the γ-keto ester B-6. The 11β-aryl group is introduced as described above and the resulting compound B-8 is hydrolyzed with acid and water, preferably trifluoroacetic acid and water with CH$_2$C$_{12}$ as a solvent, to the 17α-hydroxy ester B-9. Heating of this compound with an anhydrous acid such as preferably trifluoroacetic acid in an organic solvent such as preferably CH$_2$C$_{12}$ with removal of ethanol to drive the equilibrium towards the lactone results in the formation of the spirolactone compound, such as for example 11β-(4-(N,N-dimethylamino)phenyl)-3,20-dioxo-17α-hydroxy-19,21-dinorchola-4,9-dien-24-oic acid δ-lactone (B-10, Ar=4-Me$_2$—N— C$_6$H$_4$—).

Figure 3A:
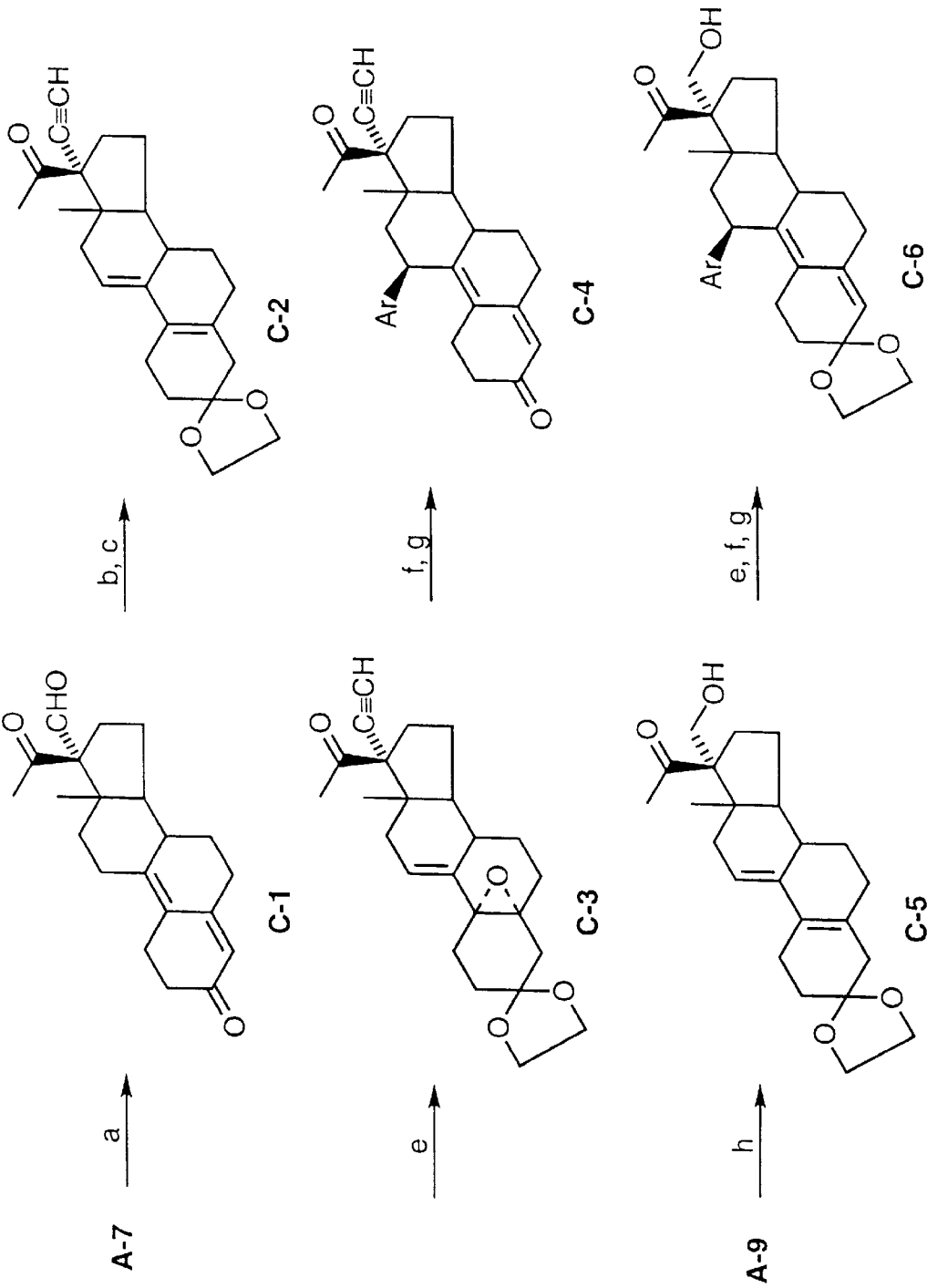
FIG. 3 illustrates a synthetic scheme for preparing 17α-ethynyl and 17α-oxymethyl substituted compounds.

Intermediate A-7 can also be used to make 11β-aryl compounds having carbon substitution such as alkynyl or oxymethyl in the 17α-position of the pregnane nucleus. Thus as shown in FIG. 3, oxidation with for example Swern reagent to the aldehyde C-1, reaction with the Seyferth-Gilbert reagent and monoketalization with for example ethylene glycol in the presence of p-toluenesulfonic acid yields the ethynyl compound C-2. Epoxidation to C-3, 11β-arylation and deketalization/dehydration as described above results in for example 11β-(4-(N,N-dimethylamino) phenyl)-17α-ethynyl-19-norpregna-4,9-diene-3,20-dione (C-4, Ar=4-Me$_2$N—C$_6$H$_4$—). The dicarbonyl compound A-9 may be selectively reduced (for example with LiAl (OBu$_t$)$_3$H), to give the versatile intermediate C-5. Compound C-5 may be converted to hydroxymethyl dienones C-6, for example 11β-(4-(N,N-dimethylamino)phenyl)-17α-hydroxymethyl-19-norpregna-4,9-diene-3,20-dione (C-6, Ar=4—Me$_2$N—C$_6$H$_4$—), by introduction of an 11βaryl moiety as described above, followed by treatment with an acid, preferably trifluoroacetic acid, and water, or may be converted to various esters such as C-8 (for example, Ar=4-Me$_2$N—C$_6$H$_4$—, R=CH$_3$ or C$_6$H$_5$) by treatment with an organic anhydride andy pyridine followed by 11β-arylation and acid treatment. Alkylation of the hydroxyl group with an alkylating agent such as for example methyl iodide or methyl triflate followed by 11β-arylation and the acid/water treatment yields a 17α-alkoxymethyl compound such as for example, 11β-(4-(N,N-dimethylamino)phenyl)-17α-methoxymethyl-19-norpregna-4,9-diene-3,20-dione (C-10, Ar=4-Me$_2$N—C$_6$H$_4$—, R=CH$_3$).

Figure 4A:
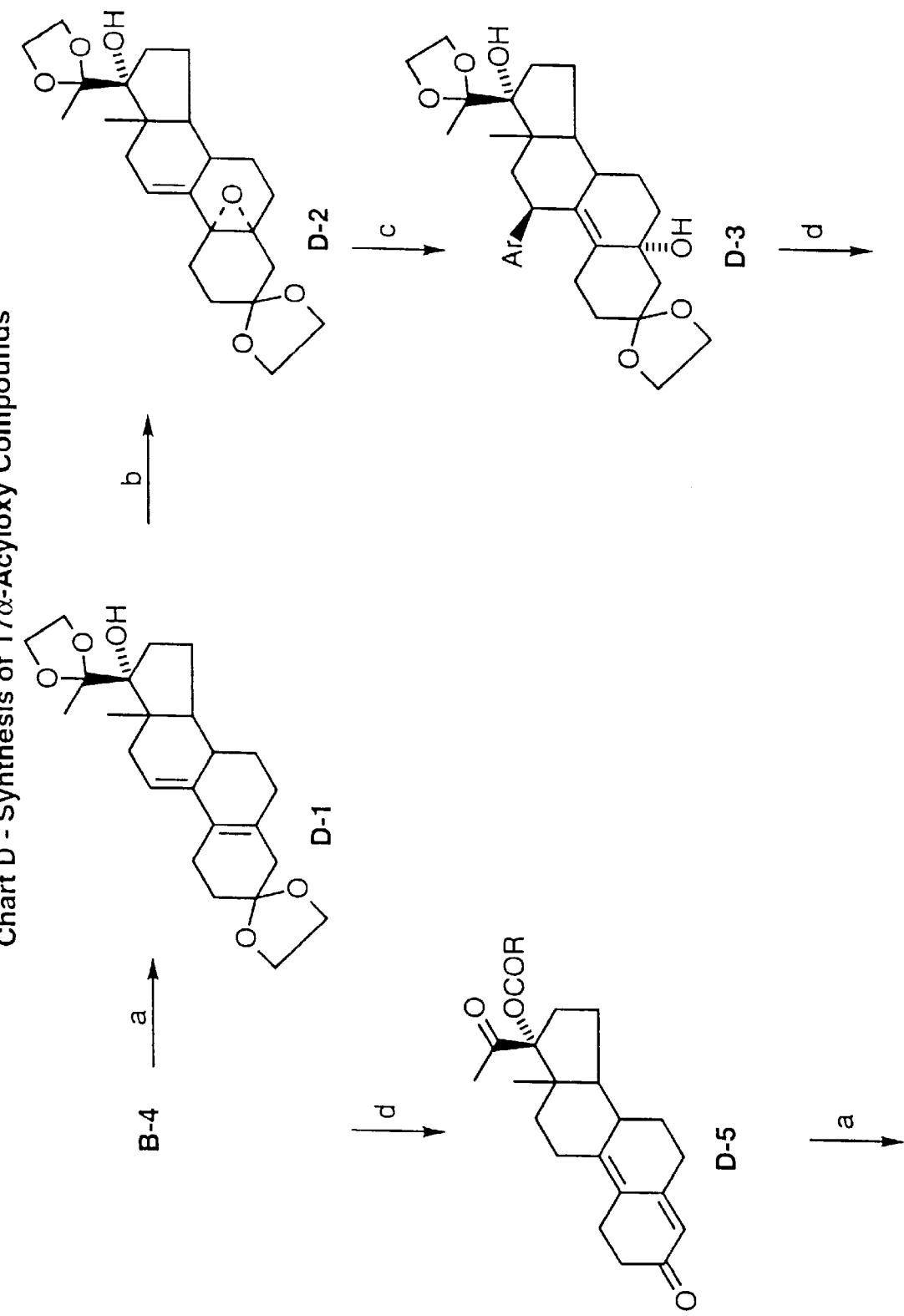
FIG. 4 illustrates a synthetic scheme for preparing 17α-acyloxy substituted compounds.
Figure 4B:
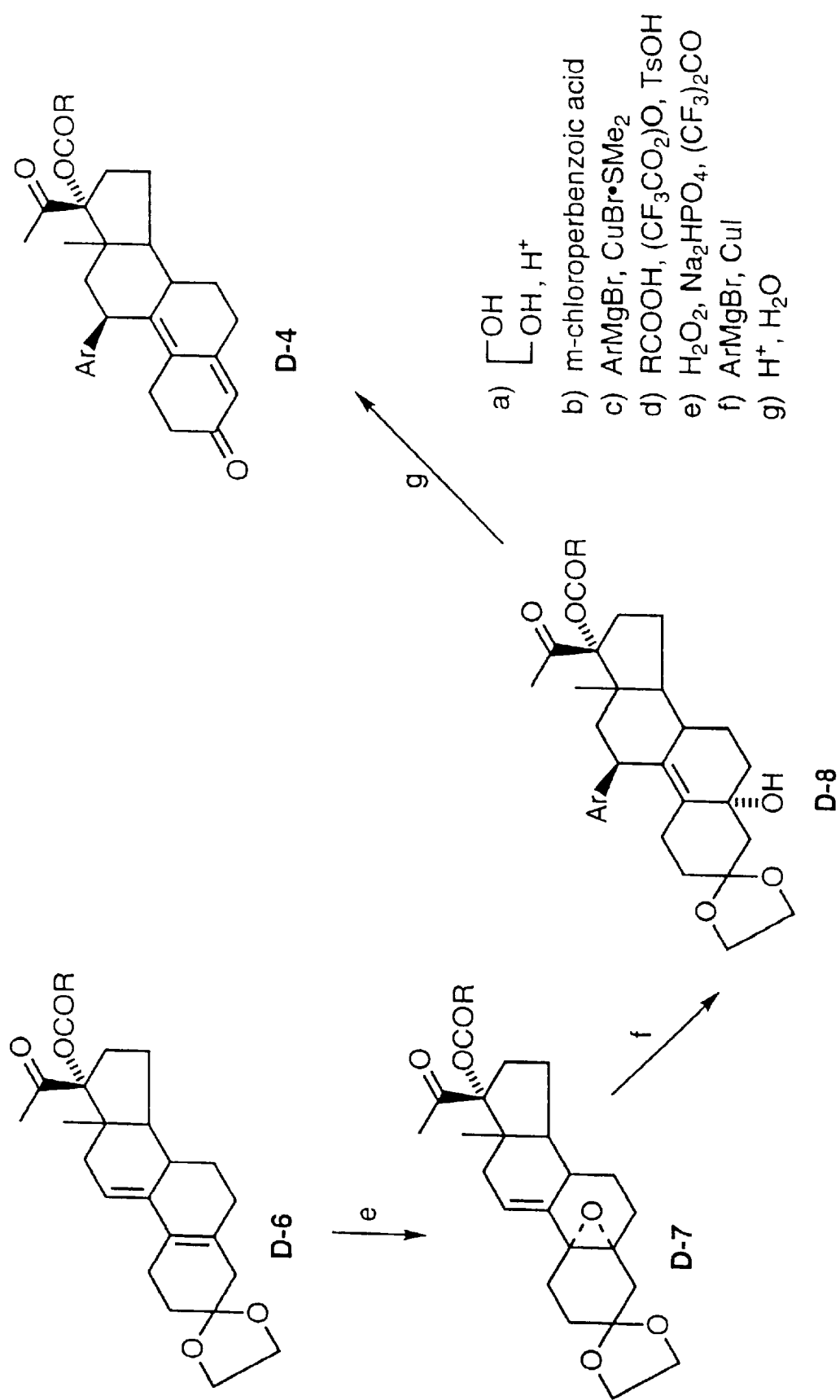

Compound B-4 can be converted to a series of 17α-acyloxy compounds D-4 as illustrated in FIG. 4, by first converting it into the diketal D-1 with for example ethylene glycol in the presence of p-toluene-sulfonic acid followed by the standard procedures of epoxidation and arylation as described above. The resulting compounds D-3 may be esterified at the C-17α-hydroxyl and deketalized/dehydrated to the desired compounds D-4 by treatment with a carboxylic acid, trifluoroacetic anhydride and p-toluenesulfonic acid. Alternatively and more preferably, compound B-4 may be converted to the 17α-acyloxy compound D-5 by treatment with a carboxylic acid, trifluoroacetic anhydride and p-toluenesulfonic acid. Selective formation of the monoketal occurs readily by reaction with ethylene glycol in the presence of p-toluenesulfonic acid to yield D-6. This compound is readily converted to the epoxide D-7 by reaction with hydrogen peroxide, hexafluoroacetone and Na$_2$HPO$_4$. Although epoxide D-7 reacts with aryl Grignard reagents that have been pretreated with CuBr/dimethyl sulfide complex, care should be taken that the Grignard reagent is not in molar excess of the copper reagent, otherwise reactions may occur that involve the D-ring substituents. Yields in this reaction are generally around 40%. Surprisingly, much better yields of product D-8 (around 60%) are obtained when CuI is used as the source of the copper. Even more surprisingly, the best yields are obtained when the CuI and epoxide D-7 are mixed together in an organic solvent, such as for example tetrahydrofuran, and the Grignard reagent in tetrahydrofuran is added rapidly to the stirred mixture at a low temperature, preferably around 0° Celsius. Thus, bu use of this latter procedure, yields of D-8 in excess of 90% can be obtained. The deketalization/dehydration of D-8 under standard conditions, preferably with trifluoroacetic acid and water, leads readily to the desired analogs D-4.

Figure 5A:
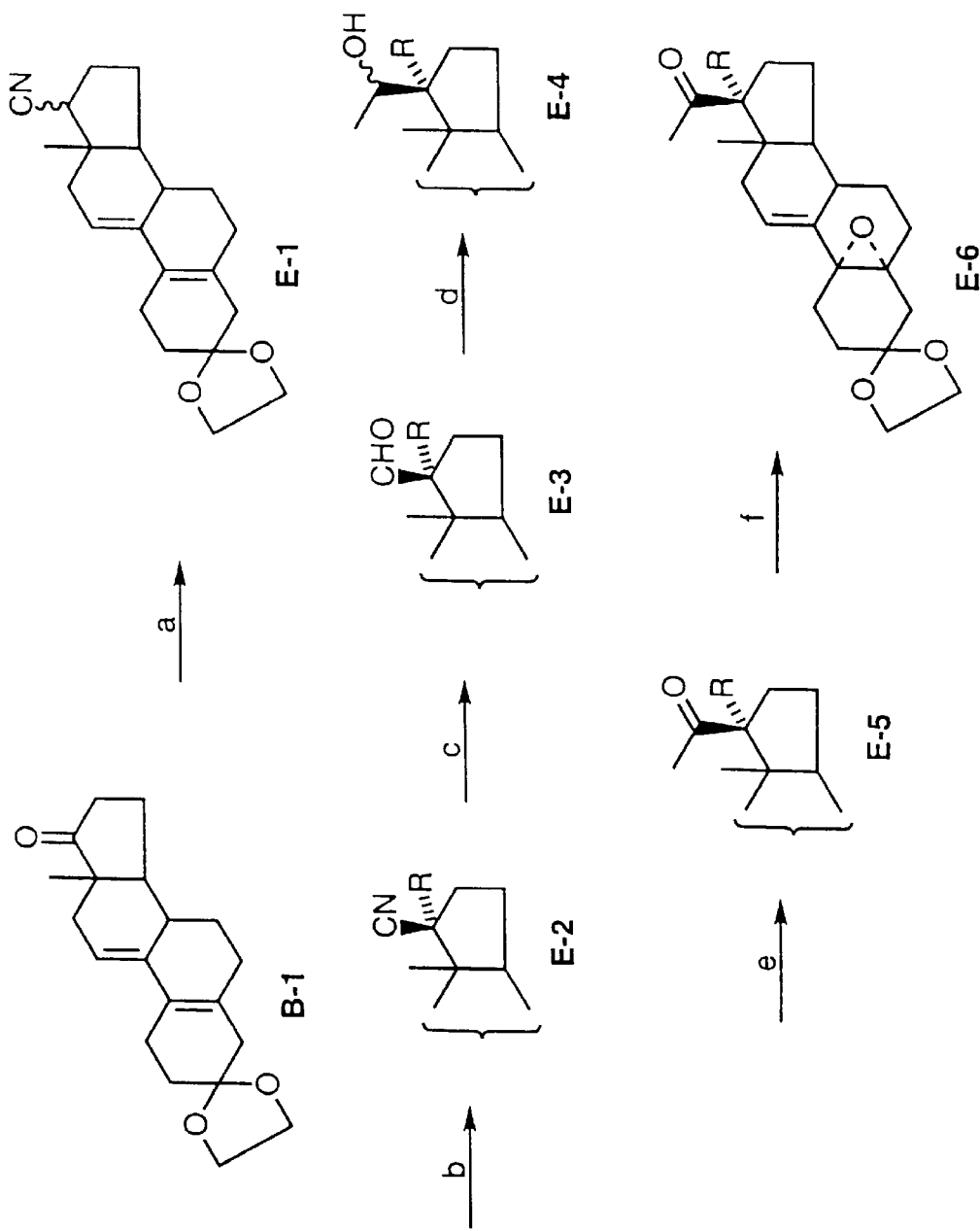
FIG. 5 illustrates a synthetic scheme for preparing 17α-alkyl substituted compounds.
Figure 5B:
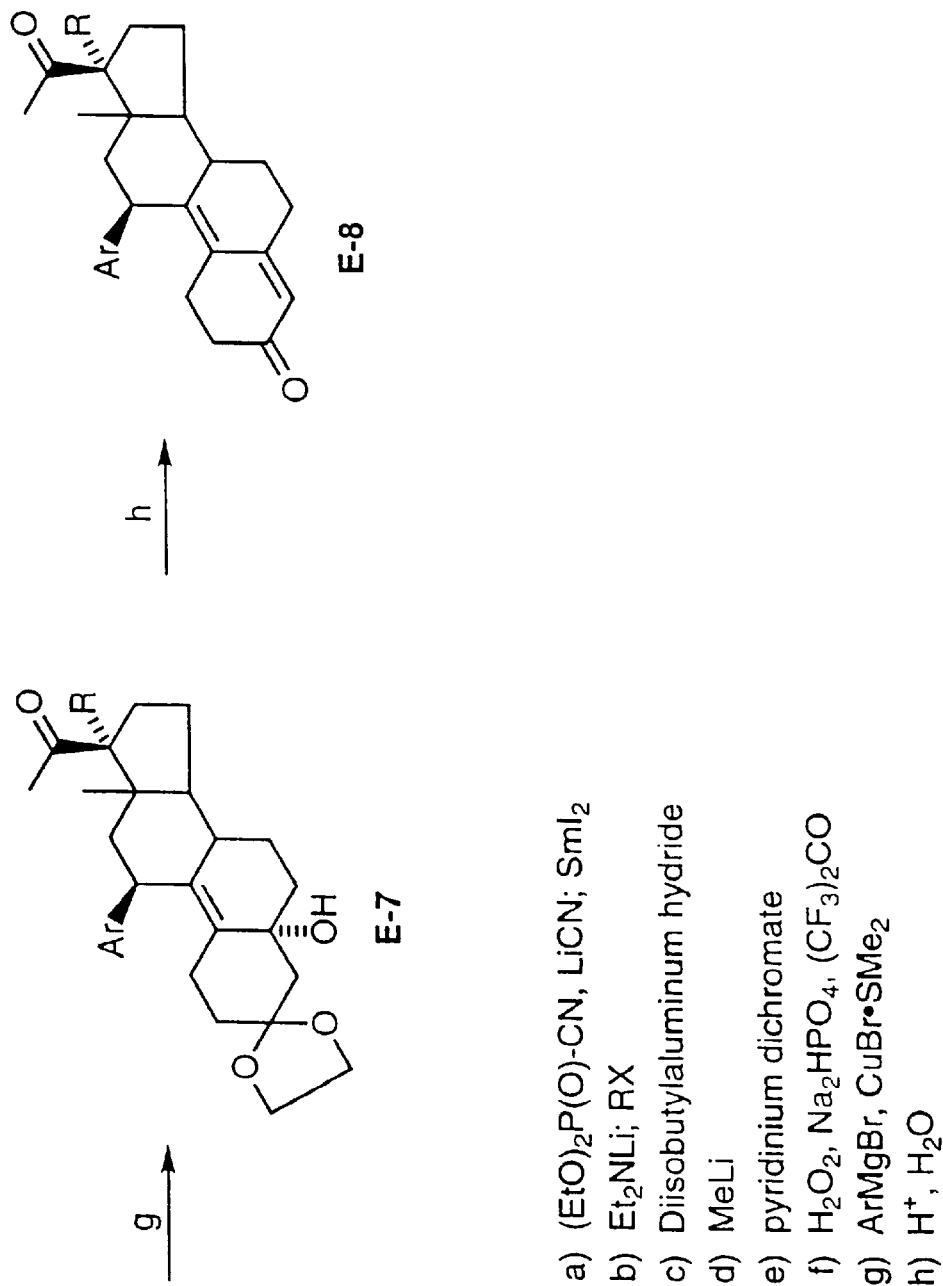

17α-carbon substituted compounds may also be obtained by following the procedure of FIG. 5. Compound B-1 is converted to the 17-cyano compound E-1 by successive treatment with $(EtO)_2P(O)CN/LiCN$ and $SmI_2$. The anion of this compound is generated by use of a metal dialkylamide such as for example lithium diethylamide and then treated with an alkylating agent, for example ethyl iodide, to yield the 17α-substituted-17β-cyano compound E-2. The cyano group is converted to 17β-acetyl by successive treatment with diisobutylaluminum hydride, methyl lithium, and pyridinium dichromate. The resulting compound E-5 is treated in the manner previously described to convert it to the epoxide E-6, the 11β-aryl intermediate E-7 and the desired final product E-8.

Compounds according to the present invention where $R^1$ is an amine or cyclic amine compound may also be prepared by converting the corresponding compound where $R^1$ is a leaving group such as halogen, or $CF_3SO_2O$—, the later prepared by conventional methods known to those of ordinary skill from the corresponding HO aryl compound, by treatment with a Pd complex in the presence of the corresponding amine compound of $R^1$. Such a procedure is known to those of ordinary skill in the art (e.g Louie et al J. Org. Chem. 62:1268–1273 (1997) and Guram et al. Angew. Chem. Int. Ed. Engl. 34:1348–1350 (1995).

The present invention also provides for a method of preparing 11β-aryl substituted steroid intermediates bearing a $C_5$ hydroxyl group by an epoxide ring opening reaction of a 5(10)α-oxido-9(11)-ene steroid with an aryl Grignard reagent ArMgX by premixing the steroid with a copper (I) salt, preferably in an organic solvent, and adding to the mixture a solution of ArMgX in an organic solvent. By premixing the epoxy steroid and copper(I) salt, improved yield of the opened product may be observed.

Suitable copper (I) salts are known to those of ordinary skill in the art such as copper iodide, copper bromide, copper chloride and copper cyanide. In a preferred embodiment copper iodide is used.

Suitable aryl Grignard reagents ArMgX, where X is a halogen atom may be prepared by conventional methods known to those of ordinary skill in the art from the corresponding aryl halide compound, by reaction with Mg. In a preferred embodiment, the Ar group of the aryl Grignard reagent is substituted at the para position with an amine group, even more preferably a piperidino group.

The reaction may be conducted in organic solvents which are known to those of ordinary skill in the art for the preparation of Grignard reagents and for formation of cuprate reagents. For example ether solvents such as diethyl ether, tetrahydrofuran and dimethyl ether may be used. Small amounts of aromatic solvents may also be used such as benzene, toluene or xylene to assist in solubilizing the reagents.

The molar ratio of steroid compound to copper salt to aryl Grignard is typically 1:1–6:1–6, preferably 1:2:4.

In one embodiment the 5(10)α-oxido-9(11)-ene steroid is substituted at the 17 position with a β-acetyl or a substituted β-acetyl group. Suitable substitutents for the 17-acetyl group are as previously described for the group $R^0$.

The compounds of the present invention bind with good affinity to the progestin receptor (Table 1) and have antiprogestational activity in vitro (Table 2) or in vivo (Tables 3,4). In contrast to current antiprogestins, these compounds have the following novel features: a 17, 17 six membered spiro lactone f unction; reversal of the 17α-OC(=O)R function to a 17α-C(C=O)OR; and a cyclic and bicyclic amino substituent on the 11-aryl moiety.

Such compounds are useful in the treatment of endometriosis, uterine leiomyomas (fibroids) and certain cancers and tumors, in hormone replacement therapy as well as in the control of various steps in reproduction and fertility, such as contraception. A more detailed description of the potential uses of such compounds is given in Donaldson, Molly S.; Dorflinger, L.; Brown, Sarah S.; Benet, Leslie Z., Editors, *Clinical Applications of Mifepristone (RU 486) and Other Antiprogestins,* Committee on Antiprogestins: Assessing the Science, Institute of Medicine, National Academy Press, 1993. They are also useful as intermediates for the synthesis of other steroids.

Having generally described this invention, a further understanding can be obtained by reference to certain specific examples which are provided herein for purposes of illustration only and are not intended to be limiting unless otherwise specified.

EXAMPLE 1

Synthesis of 17α-carbomethoxy-11β-(4-(N,N-dimethylamino)phenyl)-19-norpregna-4,9-diene-3, 20-dione (A-13, Ar=4-Me$_2$N—C$_6$H$_4$—)

17α-Hydroxymethyl-3-methoxy-19-norpregna-1,3,5(10)-trien-20-ol (A-4)

17α-Hydroxymethyl-3-methoxy-19-norpregna-1,3,5 (10)-trien-20-one (A-3, U.S. Pat. No. 4,512,986, 12.0 g, 35 mmol) in dry tetrahydrofuran (THF, 300 mL) was treated with lithium aluminum hydride (2.7 g, 71.1 mmol) at 0° C. with stirring for 1.5 hr. The reaction was quenched with Rochelle's salt solution (60 mL, saturated) and extracted with ether. Combined organic extracts were dried (MgSO$_4$) and solvent evaporated to yield the product as a mixture of C-20 epimers that were partially separated by flash column chromatography (SiO$_2$; to 10% acetone in CH$_2$Cl$_2$). Total yield was 10 g (89%). $^1$H NMR (250 MHz; CDCl$_3$) (less polar isomer) δ_7.21 (d, 1, J=8.5 Hz, 1-H), 6.75 (d, 1, J=2.75, 8.6 Hz, 2-H), 6.62 (dd, 1, J=2.7 Hz, 4-H), 3.78 (s, 3, CH$_3$O), 1.34 (d, 3, J=6.46 Hz, 21-CH$_3$), 1.01 (s, 3, 18-CH$_3$).

20-Hydroxy-17α-hydroxymethyl-3-methoxy-19-norpregna-2,5(10)-diene (A-5)

Compound A-4 (mixture of C-20 isomers; 39.0 g, 113.2 mmol) in THF (1.1 L) and t-BuOH (400 mL) was added slowly to 1.5 L of liquid NH$_3$ over 50 min at −78° C., followed by lithium wire (8.3 g, 1.20 mol). After the reaction was stirred for 3 h at −78° C., MeOH (250 mL) was cautiously added and the NH$_3$ was evaporated. Partition with saturated NH$_4$Cl, extraction of the aqueous layer with EtOAc (3×500 mL) and washing of the combined organic layers with water and brine, followed by drying (MgSO$_4$) and evaporation of solvent gave crude A-5 in 100% yield, suitable for the subsequent reaction.

20-Hydroxy-17α-hydroxymethyl-19-norpregn-5(10)-en-3-one (A-6)

Crude A-5 from above was dissolved in a mixture of THF (650 mL) and dioxane (800 mL) followed by the addition of oxalic acid (22.5 g, 250.0 mmol) in water (500 mL). The reaction was stirred at room temperature overnight and slowly quenched with dilute $NaHCO_3$ solution. The aqueous layer was extracted three times with $CH_2Cl_2$. The organic layers were combined, washed with saturated $NaHCO_3$ and brine, and dried over $MgSO_4$. The solvent was evaporated to yield the product as a white solid. Purification by flash column chromatography (1:1 EtOAc/hexanes) afforded A-6 (35.7 g) as a white solid (mixture of C-20 epimers) in 95% yield for the two steps.

20-Hydroxy-17α-hydroxymethyl-19-norpregna-4,9-dien-3-one (A-7)

Crude A-6 from above (35.5 g, 106.7 mmol) in dry pyridine (600 mL) under an inert atmosphere at −2° C. was treated with pyridinium tribromide (41.7 g, 117.3 mmol) and the reaction mixture was allowed to warm slowly to room temperature overnight. The reaction was quenched with $Na_2SO_3$. The majority of the solvent was removed in vacuo. The slurry remaining was diluted with water and extracted three times with $CH_2Cl_2$. The organic layers were combined and washed with $H_2O$, dilute $CuSO_4$, $H_2O$, and brine, then dried over $Na_2SO_4$ and the solvent evaporated to yield an orange solid. Purification by flash column chromatography on silica gel (1:1 EtOAc/hexanes up to 2:1 EtOAc/hexanes) afforded compound A-7 (22.32 g) as a white solid in an overall yield of 63%. $^1H$ NMR (250 MHz, $CDCl_3$); (less polar isomer) δ 5.67 (s, 1, 4-H), 3.97 (dd, 1, J=3.3, 8.0 Hz), 3.74 (d, 1, J=9.2 Hz), 1.33 (d, 3, J=6.47 Hz, 21-$CH_3$), 1.14 (s, 3, 18-$CH_3$); (more polar isomer) 67 5.67 (s, 1, 4-H) 3.52 (t, 1, J=3.52 Hz), 1.35 (d, 3, J=6.42 Hz, 21-$CH_3$), 0.93 (s, 3, 18-$CH_3$).

3,3-[Ethandiylbis(oxy)]-20-hydroxy-17α-hydroxymethyl-19-norpregna-5(10),9(11)-diene (A-8)

A solution of 3.60 g (11.0 mmol) of A-7 (more polar isomer), 175 mg of p-toluenesulfonic acid monohydrate, and 2.9 mL of ethylene glycol in 250 mL of benzene was placed in a 500-mL flask fitted with a Dean-Stark trap and condenser. The reaction was heated at reflux for 1 h, cooled to ambient temperature and washed with 5% $NaHCO_3$ solution. The benzene layer was filtered through Whatman 1 phase separating paper and dried ($Na_2SO_4$). Removal of the solvent and drying in vacuum afforded 3.31 g (82% yield) of ketal A-8. $^1H$ NMR (500 MHz; $CDCl_3$) δ 7.35 (bs, 1, 11-H), 3.95 (m, 4, 3-ketal), 1.31 (d, 3, 21-$CH_3$), 0.72 (s, 3, 18-$CH_3$).

3,3-[Ethandiylbis(oxy)]-19-norpregna-5(10),9(11)-dien-20-one-17α-carboxaldehyde (A-9)

A solution of oxalyl chloride (7.64 mL, 15.3 mmol, 2 M in $CH_2Cl_2$) was cooled to −55° C. in a Dry-ice isopropanol bath and a solution of 2.4 mL of dimethylsulfoxide (DMSO) in 5 mL of $CH_2Cl_2$ was added. The reaction mixture was stirred for 2 min and 2.60 g (6.95 mmol) of diol A-8 in 20 mL of $CH_2Cl_2$ was added over 5 min. The reaction mixture was stirred for 15 min and 9.70 mL of triethylamine (TEA) was added. The reaction mixture was stirred for 5 min and allowed to warm to room temperature. An additional 10 mL of TEA was added followed by 100 mL of deionized water. The phases were separated and the aqueous phase was extracted 2×50 mL of $CH_2Cl_2$. The organic phases were combined washed with water (4×30 mL) and saturated NaCl solution (30 mL). The organic phase was filtered through Whatman 1 phase separating paper and dried ($Na_2SO_4$). Removal of the solvent and drying in vacuum gave keto aldehyde A-9 as a white foam (2.14 g, 83% yield) that was homogenous by TLC. $^1H$ NMR (250 MHz; $CDCl_3$) δ 9.87 (s, 1, —CHO), 5.53 (m, 1, 11-H), 3.98 (s, 4, 3-ketal), 2.23 (s, 3, 21-$CH_3$), 0.77 (s, 3, 18-$CH_3$).

17α-Carbomethoxy-3,3-[1,2-ethandiylbis(oxy)]-19-norpregna-5(10),9(11)-dien-20-one (A-10)

Resorcinol (251 mg, 2.28 mmol) was added to a solution of A-9 (650 mg, 1.76 mmol) in 10.5 mL of dioxane and 3.5 mL of 1 M phosphate buffer (pH 3.5). A solution of $NaClO_2$ (190 mg, 2.1 mmol) in 0.70 mL of water was added with stirring over a period of 5 min. The solution was stirred an additional 20 min and poured into 150 mL of cold water. The resulting white emulsion was extracted 2×75 mL and 2×50 mL of EtOAc. The combined extracts were washed with 25 mL of saturated NaCl solution and filtered through Whatman 1 phase separating filter paper. Methanol (20 mL) was added to the filtrate followed by 1.14 mL of 2 M (trimethylsilyl) diazomethane solution in hexanes. The solution was stirred for 2.5 h when TLC analysis of an aliquot workup indicated the reaction was complete. Evaporation of the solvent afforded 0.80 g of crude product. The crude product was purified by chromatography on a 5.9×72 cm Sephadex LH20 column eluted with MeOH. Fractions containing pure A-10 were combined and evaporated to afford 315 mg of pure product. $^1H$ NMR (250 MHz; $CDCl_3$) δ 5.56 (s, 1, 11-H), 3.98 (bs, 4, 3-ketal) 3.68 (s, 3, —$COOCH_3$), 2.23 (s, 3, 21-$CH_3$), 0.72 (s, 3, 18-$CH_3$).

17α-Carbomethoxy-5(10)-epoxy-3,3-[1,2-ethandiylbis(oxy)]-19-norpregn-9(11)-en-20-one (A-11)

Methyl ester A-10 (295 mg, 0.74 mmol) was dissolved in methylene chloride (2.2 mL) at 0° C. Sodium monohydrogenphosphate (73 μL of a 10 mg/mL aqueous solution, 0.734 mg, 0.0052 mmol), hexafluoroacetone trihydrate (112 μL, 0.177 g, 0.80 mmol), and 30% $H_2O_2$ solution in $H_2O$ (159 μL) were added and the reaction mixture was stirred vigorously overnight. The reaction mixture warmed slowly to 14° C. overnight. The reaction mixture was diluted with methylene chloride (30 mL), washed with cold (0–5° C.) 5% NaCl solution (15 mL) and filtered through Whatman 1 phase separating filter paper. The solvents were evaporated from the filtrate to yield a white foam (279 mg) which was purified by column chromatography. Most of the white foam (254 mg) was chromatographed on silica gel 60 for column chromatography (5 g, 230–400 mesh) that had been slurried with acetone/methylene chloride (5:95, v/v) and packed in a 1.3 cm diameter column. A mixture of 5(10)α- and β-epoxides (119.6 mg) was eluted with acetone/methylene chloride (5:95, v/v) in the 12 to 24 mL fraction. A pilot chromatography yielded another 13.1 mg for a total weight of 132.7 mg of 5(10)α- and β-epoxides. TLC: silica gel 60 F-254 developed with acetone/methylene chloride (5:95, v/v) $R_f$0.36 for the 5(10)α-epoxide and 0.39 for the 5(10) β-epoxide (minor spot). $^1H$ NMR (250 MHz; $CDCl_3$) (α-isomer) δ 6.02 (m, 1, 11-H), 3.93 (m, 4, 3-ketal), 3.68 (s, 3, $COOCH_3$), 2.51 (s, 3, 21-$CH_3$), 0.73 (s, 3, 18-$CH_3$); (β-isomer) δ 5.85 (m, 11-H, 2.46 (s, 21-$CH_3$), 0.71 (s, 18-$CH_3$).

17α-Carbomethoxy-11β-[4-(N,N-dimethylamino)phenyl]-3,3-[1,2-ethandiylbis(oxy)]-5α-hydroxy-19-norpreg-9-en-20-one (A-12, Ar=4-$Me_2N$—$C_6H_4$—)

Under anhydrous conditions in an argon atmosphere, magnesium turnings (545 mg, 41.4 mmol) were placed in a 50-mL three-neck round-bottom flask fitted with a magnetic stirbar, an addition funnel, stopper and reflux condenser topped with an argon inlet adapter. Tetrahydrofuran (5 mL, freshly distilled from sodium/benzophenone) was added to the reaction flask. 4-Bromo-N,N-dimethylaniline (3.20 g, 16 mmol) and 1,2-dibromoethane (280 μL, 3.25 mmol) were dissolved in tetrahydrofuran (4 mL) and placed in the addition funnel. One mL of this solution was added rapidly to the vigorously stirred magnesium turnings. The reaction initiated with gentle heating. The remaining 4-bromo-N,N-dimethylaniline/1,2-dibromoethane solution was added dropwise at a rate to maintain reflux. After the addition was completed and the vigorous reaction subsided, a crystal of iodine was added and the reaction mixture was refluxed for 2.25 h to yield an olive green solution with some unreacted Mg remaining. The reaction mixture was cooled to room temperature and diluted to 20 mL with tetrahydrofuran to provide a stock solution of Grignard reagent. Two mL of this stock solution was added to a 50-mL three-neck, round-bottom flask containing cuprous bromide dimethylsulfide complex (320 mg, 1.56 mmol). A thick heterogeneous slurry resulted that was diluted with three mL of tetrahydrofuran. After 15 min at room temperature, the resulting pale green slurry was cooled to −10° C. Epoxide A-11 (132 mg, some β-epoxide was present) was dissolved in tetrahydrofuran (2.5 mL) and added to the pale green slurry along with 0.5 mL of tetrahydrofuran rinse. The reaction mixture was stirred at −10° C. for 1.5 h and allowed to slowly warm to room temperature overnight. After 40 h at room temperature the reaction mixture was poured into saturated ammonium chloride solution and stirred for 45 min. The reaction mixture was extracted with methylene chloride. The extract was washed with saturated ammonium chloride solution (50 mL), dried over $MgSO_4$ (30 min, stirred magnetically) and filtered through Whatman 1 phase separating filter paper. The solvents were evaporated from the filtrate to yield 170 mg of crude product that was chromatographed on Sephadex LH-20 eluted with methanol. The desired A-12 (Ar=4-$Me_2N$—$C_6H_4$—, 25.9 mg, 0.048 mmol) of reasonable purity was eluted in the 1500 to 1600 mL fraction. $^1$H NMR (250 $MH_3$; $CDCl_3$) δ 7.6 (d, 2, Ar—H), 6.64 (d, 2, Ar—H), 4.22 (m, 1, 11-H), 3.71 (s, 3, $COOCH_3$), 2.90 [s, 6, $N(CH_3)_2$], 2.17 (s, 3, 21-$CH_3$), 0.42 (s, 3, 18-$CH_3$).

17α-Carbomethoxy-11β-[4-(N,N-dimethylamino)phenyl]-19-norprega-4,9-diene-3,20-dione (A-13, Ar=4-$Me_2N$—$C_6H_4$—)

Compound A-12 (25.9 mg, 0.048 mmol) was dissolved in two mL of hydrochloric acid in methanol prepared by adding two drops of concentrated hydrochloric acid to 10 mL of methanol. The reaction mixture was stirred magnetically at room temperature for 45 min. Twenty milligrams of sodium bicarbonate solution was added to the reaction mixture. The reaction solvents were evaporated and the residue was redissolved in methylene chloride (0.4 mL) and chromatographed on silica gel 60 for column chromatography (0.4 g, 230–400 mesh) that had been slurried with acetone/methylene chloride (3:7, v/v) and packed in a 5-mL disposable pipette. High purity A-13, by TLC analysis, was eluted with acetone/methylene chloride (3:7, v/v) in the 2.8 mL to 5.6 mL fraction. HPLC analysis on a RP-18 column (YMC, Inc. 55 120A ODS 4.6×150 mm) eluted with deionized water/methanol (2:8, v/v) at a flow rate of 1 mL/min with 254 nm with UV detection indicated 84.7% desired product ($R_t$ 4.82 min) and 14.3% unknown impurity ($R_t$ 5.16 min). Purification by preparative HPLC yielded A-13 (Ar=4-$Me_2N$—$C_6H_4$—) (4.9 mg, 20.8%) which was 99% pure by HPLC. $^1$H NMR ($CDCl_3$; 25 MHz) δ 7.01 (d, 2, Ar—H); 6.65 ([d, 2, Ar—H), 5.75 (s, 1, 4-H), 4.34 (m, 1, 11-H), 3.73 (s, 3, $COOCH_3$), 2.91 (s, 6, $N(CH_3)_2$); mass spectrum (70 eV) m/z (rel. intensity) 475.2723.

EXAMPLE 2

Synthesis of 11β-[4-(N,N-dimethylamino)phenyl]-3,20-dioxo-17α-hydroxy-19,21-dinorchola-4,9-dien-24-oic acid δ-lactone (B-10, Ar=4-$Me_2N$—$C_6H_4$—)

17α-Cyano-3,3-[1,2-ethanediylbis(oxy)]-estra-5(10),9(11)-dien-17α-ol (B-2)

To a suspension of 100 g (0.318 mol) of B-1 and 227.7 g (3.5 mol) of KCN in 1800 mL of methanol at room temperature was added 180 mL (3.18 mol) of acetic acid dropwise very slowly, especially the first 5 equivalents (90 mL), over a 3 h period. The suspension gradually became clear then turned increasingly milky white as the 17β-cyano product precipitated out of solution. The reaction mixture was allowed to stir for 3 h, poured into 12 L of ice-water, and allowed to stand overnight. Analysis by TLC (1:2 EtOAc/hexane) showed spot to spot conversion. The product was collected, washed with 1% acetic acid solution and water, and dried to afford 96.41 g, (89% yield) of a white powdery solid which was used in the next step without purification. The $^1$H NMR spectrum of B-2 was consistent with its structure: $^1$H NMR (250 MHz; $CDCl_3$) δ 5.60 (bs, 1, 11-H), 4.0 (s, 4, 3-ketal), 0.91 (s, 3, 18-$CH_3$).

17β-Cyano-3,3-[1,2-ethanediylbis(oxy)]-17α-trimethylsilyloxyestra-5(10),9(11)-diene (B-3)

To a suspension of 96.41 g (0.283 mol) of B-2 in 3.0 L of toluene at room temperature was added 395 mL (3.113 mol) of trimethylsilyl chloride (TMSCL) in one portion followed by 265 mL (3.255 mol) of pyridine added dropwise. The tan reaction solution was brought to 60° C. and allowed to stir overnight. Analysis by TLC (1:2 EtOAc/hexane) showed the major product B-3 and a trace of starting material. The reaction mixture was allowed to cool and poured over ice (2 L). The product was extracted with toluene. The organics were dried over $MgSO_4$, filtered, evaporated, and dried to afford B-3 as a yellow residue (116.9 g) in almost quantitative yield. Compound B-3 was used in the next step without purification. $^1$H NMR (250 MHz; $CDCl_3$) δ 5.38 (bs, 1, 11-H), 3.74 (s, 4, 3-ketal), 0.66 (s, 3, 18-$CH_3$), 0.10 [s, 9, $(CH_3)_3Si$].

3,3-[1,2-Ethanediylbis(oxy)]-17α-hydroxy-19-norpregna-5(10),9(11)-dien-20-one (B-4)

To a solution of 112.8 g (0.27 mol) of B-3 in 855 mL of anhydrous toluene and 255 mL of dry tetrahydrofuran (THF) under argon was added 806 mL of methylmagnesium bromide (1.4 M in 3:1 toluene/THF, 1.13 mol) in one portion. The dark green solution was brought to reflux and allowed to reflux for 16 h. The reaction mixture was allowed to cool to room temperature, and then was poured over 2.0 L of cold 10% aqueous $NH_4Cl$ solution. The organic phase was separated and the aqueous phase was extracted twice with toluene. The combined organic extracts were washed with HCl solution (1:99 concentrated aqueous HCl/water) until the aqueous phase was pH 5 and immediately washed with a 2.5% solution of $NaHCO_3$ until basic. After washing with brine, the solution was dried over $MgSO_4$, filtered, evaporated, and dried to give a crude residue (55 g). Re-extraction of the washes yielded another 21 g. Purification by silica gel chromatography with isocratic elution (hexane/EtOAc/$CH_2Cl_2$, 31:8:1) afforded 45.1 g (46.7% yield) of B-4 as a pure white solid. $^1$H NMR (250 MHz; $CDCl_3$) δ 5.57 (br s, 1, 11-H), 3.98 (s, 4, 3-ketal), 2.83 (s, 1, —OH), 2.27 (s, 3, 21-$CH_3$), 0.69 (s, 3, 18-$CH_3$).

3,3-[1,2-Ethanediylbis(oxy)]-17α-trimethylsilyloxy-19-norpregna-5(10),9(11)-dien-20-one (B-5)

Under argon at room temperature, B-4 (45 g, 0.126 mol) and triethylamine (77.5 mL, 0.56 mol) in $CH_2Cl_2$ (500 mL) were stirred and treated with trimethylsilyl triflate (25.86 mL, 0.14 mol). At 2 h and 3.75 h, more triethylamine (16 mL) and trimethylsilyl triflate (6 mL) were added. After 5 h, the reaction mixture was poured into 5% sodium bicarbonate solution (700 mL). Phases were separated and the aqueous phase was re-extracted with $CH_2Cl_2$ (2×350 mL). The extract was washed with deionized water (2×500 mL) and with saturated NaCl (500 mL) and filtered. Solvents were evaporated and the residue dried overnight in vacuo at room temperature. Isocratic chromatography on silica gel with hexane/CH$_2$Cl$_2$ (25:75) gave B-5 (39 g, 72% yield). $^1$H NMR (CDCl$_3$, 250 MHz) δ 5.60 (br s, 1, 11-H), 3.99 (s, 4, 3-ketal), 2.15 (s, 3, 21-CH$_3$), 0.53 (s, 3, 18-CH$_3$), 0.11 [s, 9, —O—Si(CH$_3$)$_3$].

3,3-[1,2-Ethanediylbis(oxy)]-20-oxo-17α-trimethylsilyloxy-19,21-dinorchola-5(10),9(11)-dien-24-oic acid ethyl ester (B-6)

Under argon, THF (348 mL, freshly distilled from sodium/benzophenone) and N-tert-butyltrimethylsilylamine (43.5 mL, 228 mmol) were cooled to 0–5° C. and n-butyllithium (250.8 mmol, 50.2 mL of 2.5 M solution in hexanes) was added over 10 min and the solution kept 1.5 h at 0–5° C. TMS ether B-5 (39 g, 92 mmol) in THF (250 mL) was cooled to −78° C. under argon. After 10 min, half of the lithium amide solution was added over 10 min. After an additional 10 min, ethyl bromoacetate (50 mL, 450 mmol) was added over 5 min. The reaction mixture was kept at −78° C. for 4 h and allowed to slowly warm to room temperature overnight. It was then poured into cold dilute NaHCO$_3$ solution (2 L of deionized water and 40 mL of 5% NaHCO$_3$ solution) and extracted with EtOAc (3×500 mL). The extract was washed with deionized water (3×500 mL) and saturated NaCl (500 mL) and dried by stirring with sodium sulfate for several hours. Filtration and solvent evaporation yielded a dark orange oil (66 g) that was dissolved in CH$_2$Cl$_2$ (100 mL) and chromatographed on silica gel with hexane/EtOAc/CH$_2$Cl$_2$ (8:1:1, v:v:v). Rechromatography of mixed fractions gave a total of 30.0 g of pure B-6 and 10.2 g of B-5. Based on B-5 consumed, the yield of B-6 was 86.6%. $^1$H NMR (CDCl$_3$, 250 MHz) δ 6.09 (br s, 1, 11-H), 4.14 (q, 2, J=7.1 Hz, —CH$_2$—CH$_3$), 3.99 (s, 4, 3-ketal), 1.26 (t, 3, J=7.1 Hz, —CH$_2$—CH$_3$), 0.52 (s, 3, 18-CH$_3$), 0.12 [s, 9, O—Si(CH$_3$)$_3$].

3,3-[1,2-Ethanediylbis(oxy)]-5(10)α-epoxy-20-oxo-17α-trimethylsilyloxy-19,21-dinorchol-9(11)-en-24-oic acid ethyl ester (B-7) and 11β-[4-(N,N-Dimethylamino)phenyl]-3,3-[1,2-ethanediylbis(oxy)]-5α-hydroxy-20-oxo-17α-trimethylsilyloxy-19,21-dinorchol-9-en-24-oic acid ethyl ester (B-8, Ar=4-Me$_2$N—C$_6$H$_4$—)

Na$_2$HPO$_4$ (1.49 g, 10.51 mmol), hexafluoroacetone trihydrate (9.1 mL, 65.4 mmol) and 30% H$_2$O$_2$ solution in H$_2$O (13.5 mL) were stirred with CH$_2$Cl$_2$ (66 mL) at 0° C. until the salt was completely dissolved. The mixture was then added in one portion to a stirred solution of B-6 (27.7 g, 53.7 mmol) in CH$_2$Cl$_2$ (329 mL) at 0° C. The reaction mixture was stirred vigorously at 0–5° C. overnight. It was then diluted with 700 mL of cold (0–5° C.) CH$_2$Cl$_2$, washed with cold 0.05% NaHCO$_3$ solution (500 mL), cold 5% Na$_2$S$_2$O$_3$ solution (500 mL) containing 5% sodium bicarbonate solution (10 mL), cold deionized water (500 mL) and cold saturated NaCl (500 mL), dried over Na$_2$SO$_4$, and filtered. Evaporation and drying yielded crude B-7 (27.4 g), used without further purification.

Under argon, a Grignard reagent was prepared from magnesium (6.13 g, 0.25 mol) and 4-bromo-N,N-dimethylaniline (45.38 g, 0.23 mol) in THF (241 mL, freshly distilled from sodium/benzophenone) with 1,2-dibromethane (1.00 mL, 11.6 mmol) as an initiator. Under nitrogen, CuBr·dimethyl sulfide complex (47.2 g, 0.23 mol) and THF (241 mL, freshly distilled from sodium/benzophenone) were stirred while the Grignard solution was added dropwise at room temperature over 30 min. After the slurry had been stirred for 2 h longer at room temperature, it was cooled to −5° C.; and crude epoxide B-7 (29.3 g, from 58.1 mmol of B-6) dissolved in THF (250 mL) was added over 30 min. After 15 min longer at −5 ° C., the reaction mixture was allowed to slowly warm to room temperature overnight. It was then poured into saturated NH$_4$Cl solution (1.5 L); and the resulting mixture was stirred vigorously for 2 h. Deionized water (1 L) was added, and the resulting emulsion was extracted with methylene chloride (3×700 mL). The extract was washed with deionized water (2×700 mL), saturated NaCl solution (700 mL), and filtered. Evaporation and drying followed by chromatography on silica gel with hexane/EtOAc/CH$_2$Cl$_2$ (60:40:5, v:v:v) gave B-8 (22.3 g, 59.2% from B-6). $^1$H NMR (CDCl$_3$, 250 MHz) δ 7.04 [d, 2, J=8.7 Hz, Ar—H meta to N(CH$_3$)$_2$] 6.62 [d, 2, J=8.7 Hz (Ar—H ortho to N(CH$_3$)$_2$], 4.45 (s, 1, 5-OH), 4.27 (m, 1, 11-H), 4.12 (q, 2, J=7.1 Hz, CH$_2$CH$_3$), 3.88–4.08 (m, 4, 3-ketal), 2.89 [s, 6, N(CH$_3$)$_2$], 1.24 (t, 3, J=7.1 Hz, CH$_2$CH$_3$), 0.20 (s, 3, 18-CH$_3$), 0.13 [s, 9, O—Si(CH$_3$)$_3$].

11β-[4-(N,N-Dimethylamino)phenyl]-3,20-dioxo-17α-hydroxy-19,21-dinorchola-4,9-dien-24-oic acid ethyl ester (B-9, Ar=4-Me$_2$N—C$_6$H$_4$)

B-8 (10.9 g, 16.8 mmol) in CH$_2$Cl$_2$ (250 mL) at 0–5° C. and deionized water (604 μL, 33.6 mmol) were stirred vigorously while trifluoroacetic acid (21 mL, 273 mmol) was added dropwise over 5–10 min. The reaction flask was flushed with argon, stoppered, and allowed to slowly warm to room temperature overnight. Then solvents were evaporated and the resulting residue was evaporated in vacuo. Methylene chloride was twice added, and the evaporation procedure was repeated. After a final evaporation time of 1.25 h in vacuo, the resulting crude product B-9, isolated as the trifluoroacetate salt (Ar=4-Me$_2$N—C$_6$H$_4$, a dark brown oil) was found by TLC analysis to be fairly pure and was used to synthesize B-10 (Ar=4-Me$_2$N—C$_6$H$_4$) without further purification. For characterization purposes, the crude product was partitioned between Na$_2$CO$_3$ and CH$_2$Cl$_2$ before being purified by column chromatography on silica gel with hexane/EtOAc/CH$_2$Cl$_2$ (60:40:5, v:v:v). $^1$H NMR (CDCl$_3$, 250 MHz) δ 6.99 [d, 2, J=8.8 Hz, Ar—H, meta to N(CH$_3$)$_2$], 6.63 [d, 2, J=8.8 Hz, Ar—H, ortho to N(CH$_3$)$_2$], 5.75 (s, 1, 4-H), 4.36 (m, 1, 11-H), 4.12 (q, 2, J=7.1 Hz, —CH$_2$CH$_3$), 2.90 [s, 6, N(CH$_3$)$_2$], 1.24 (t, 3, J=7.1 Hz, CH$_2$—CH$_3$), 0.40 (s, 3, 18-CH$_3$). IR (CH$_2$Cl$_2$) 3490 (17α-hydroxyl), 2935 (saturated hydrocarbon), 1729 (ester carbonyl), 1703 (20-carbonyl), 1655 (3-carbonyl), 1606 cm$^{-1}$ (diene); mass spectrum (70 eV), m/z (rel intensity) 519 (7), 473 (8), 389 (10), 121 (100), C$_{32}$H$_{41}$NO$_5$ requires an M$^+$ at m/z 519.

11β-[4-(N,N-Dimethylamino)phenyl]-3,20-dioxo-17α-hydroxy-19,21-dinorchola-4,9-dien-24-oic acid δ-lactone (B-10, Ar=4-Me$_2$N—C$_6$H$_4$)

Under argon, crude B-9 (Ar=4-Me$_2$N—C$_6$H$_4$ from 10.9 g of B-8) was dissolved in CH$_2$Cl$_2$ (300 mL). Trifluoroacetic acid (46 mL) was added, and the stirred reaction mixture was refluxed overnight. The next morning the reaction solvents were evaporated. CH$_2$Cl$_2$ was twice added and evaporated. The resulting residue was further dried for 15 min in vacuo before fresh reagents (300 mL of CH$_2$Cl$_2$ and 46 mL of trifluoroacetic acid) were added and the overnight reflux repeated. The reaction solvents were evaporated. The resulting residue was dried, fresh reagents were added, and the overnight reflux was repeated. This overall process was done another three times. After the final evaporation of reaction solvents, the resulting residue was redissolved in CH$_2$Cl$_2$ (300 mL) and poured into dilute sodium bicarbonate solution (pH of aqueous phase was 8). The phases were mixed and separated, and the aqueous phase was re-extracted with methylene chloride (2×200 mL). The extract was washed with deionized water (300 mL) and saturated NaCl (300 mL) and filtered. Evaporation of the solvent left a foam that was dissolved in CH$_2$Cl$_2$ (50 mL)

and chromatographed on silica gel with a stepwise gradient of 11 L of hexane/EtOAc/$CH_2Cl_2$ (5:5:1, v:v:v), 4 L of hexane/EtOAc/$CH_2Cl_2$ (4:6:1, v:v:v), 1.6 L of hexane/EtOAc/$CH_2Cl_2$ (3:7:1, v:v:v) and 1 L of hexane/EtOAc/$CH_2Cl_2$ (2:8:1, v:v:v) to yield spirolactone B-10 (Ar=4-$Me_2N$—$C_6H_4$) [4.54 g, 65.9% based on consumed B-8 (1.4 g recovered)]. The compound was dried at 100° C. for 4 h in a vacuum oven to remove the solvents. The resulting spirolactone B-10 (Ar=4-$Me_2N$—$C_6H_4$ (3.66 g) was a light yellow solid that was shown to be >99% pure by high performance liquid chromatography (HPLC) analysis. $^1$H NMR ($CDCl_3$, 250 MHz) δ 6.96 [d, 2, J=8.8 Hz, Ar—H meta to $N(CH_3)_2$], 6.63 [d, 2, J=8.8 Hz, Ar—H ortho to $N(CH_3)_2$], 5.76 (s, 1, 4H), 4.39 (m, 1, 11-H), 2.91 [s, 6, N(—$CH_3$)$_2$], 0.52 (s, 3, 18-$CH_3$); IR ($CH_2Cl_2$) 2935 (saturated hydrocarbon), 1740 (ester carbonyl), 1718 (20-carbonyl), 1657 (3-carbonyl), 1608 $cm^{-1}$ (diene); mass spectrum (70 eV) m/z (rel intensity) 473 (35), 121 (100), $C_{30}H_{35}NO_4$ requires an $M^+$ at m/z 473. An analytical sample prepared by preparative HPLC [RP-18, deionized water/acetonitrile (1:1, v:v)] and dried in the presence of Drierite® at 81–82° C. in vacuo for 72 h was shown to be partially hydrated by $^1$H NMR analysis. Anal. Calcd for $C_{30}H_{35}NO_4$.0.25 $H_2O$: C, 75.41; H, 7.49; N, 2.93. Found: C, 75.57; H, 7.45; N, 2.93.

EXAMPLE 3

Synthesis of 11β-(4-(N,N-dimethylamino)phenyl-17α-ethynyl-19-norpregna-4,9-diene-3,20-dione (C-4, Ar=4-$Me_2N$—$C_6H_4$)

17α-Formyl-19-norpregna-4,9-diene-3,20-dione (C-1)

Oxalyl chloride (31.8 mL, 63.6 mmol) in $CH_2Cl_2$ (10 mL) was cooled under an inert atmosphere to –60° C. Dimethylsulfoxide (DMSO, 6.0 mL, 84.6 mmol) was added dropwise and the reaction was stirred for 30 min followed by the slow addition of compound A-7 (7.0 g, 21.2 mmol; mixture of isomers) in dry $CH_2Cl_2$ (44 mL). The reaction was stirred for 30 min at –60° C. $Et_3N$ (19.5 mL, 140.0 mmol) was then added and the mixture stirred for 20 min at –60° C. and then slowly warmed to room temperature over 1 h. The reaction was quenched with $H_2O$, extracted three times with $CH_2Cl_2$, and washed with $H_2O$ and brine. The organic layer was dried over $MgSO_4$, and the solvent removed in vacuo to yield a brown oily solid, used without purification in the next step. $^1$H NMR (250 MHz; $CDCl_3$) δ 9.84 (s, 1, formyl-H), 5.68 (s, 1, 4-H), 2.34 (s, 3, 21-$CH_3$), 0.96 (s, 3, 18-$CH_3$).

3,3-[1,2-Ethanediylbis(oxy)]-17α-ethynyl-19-norpregna-5(10),9(11)-dien-20-one (C-2)

t-BuOK (3.08 g, 25.2 mmol) in dry THF (50 mL) and $(CH_3O)_2POCHN_2$ (3.7 8 g, 25.18 mmol; Seyferth/Gilbert reagent) in dry THF (25 mL) were cooled under an inert atmosphere to –78° C. The Seyferth/Gilbert reagent was then treated slowly with the t-BuOK solution and stirred for 10 min at –78° C. Compound C-1 from the above reaction (assumed 19.0 mmol) in dry THF (80 mL) was added slowly. The reaction was stirred at –78° C. and then slowly warmed to room temperature overnight, quenched with $H_2O$ and extracted four times with $CH_2Cl_2$. The organic layers were combined, washed with brine, and dried over $MgSO_4$. The solvent was evaporated and the residue purified by flash silica gel column chromatography (1:1 EtOAc/hexanes) to give a solid (4.98 g) that was dissolved in benzene (300 mL) and treated with ethylene glycol (11.8 mL, 212 mmol) and p-toluenesulfonic acid (330 mg, 1.74 mmol). The reaction was heated to reflux for 1.5 h, cooled to room temperature and quenched with aqueous $NaHCO_3$. The aqueous layer was extracted twice with EtOAc. The organic layers were combined, washed with $H_2O$ and brine, and dried over $MgSO_4$. The solvent was evaporated to leave a yellow solid that was purified by silica gel flash column chromatography (1:1 EtOAc/hexanes) afforded the desired product C-2 (69% yield from C-1). $^1$H NMR (250 MHz; $CDCl_3$) δ 5.60 (bs, 1, 11-H), 4.04 (s, 4, 3-ketal), 2.43 (s, 1, ethynyl-H), 2.31 (s, 3, 21-$CH_3$), 0.59 (s, 3, 18-$CH_3$).

11β-(4-(N,N-Dimethylamino)phenyl)-17α-ethynyl-19-norpregna-4,9-diene-3,20-dione (C-4, Ar=4-$Me_2N$—$C_6H_4$)

By the methods described above for the synthesis of 11β-(4-(N,N-dimethylamino)phenyl)-3,20-dioxo-17α-hydroxy-19,21-dinorchola-4,9-dien-24-oic acid δ-lactone (B-10, Ar=4-$Me_2N$—$C_6H_4$—), compound C-2 is converted to the epoxide C-3 and then to the title compound C-4, (Ar=4-$Me_2N$—$C_6H_4$). $^1$H NMR (250 MHz; $CDCl_3$) δ 7.28 (d, 2, Ar—H), 6.99 (d, 2, Ar—H), 5.76 (s, 1, 4-H), 4.40 (d, 1, 11-H), 2.91 [s, 6, N($CH_3$)$_2$], 2.33 (s, 1, CC≡C—H) 0.33 (s, 3, 18-$CH_3$).

EXAMPLE 4

Synthesis of 17α-Acetoxy-11β-[4-(N-piperidino)phenyl]-19-norpregna-4,9-diene-3,20-dione (D-4, R=$CH_3$, Ar=4-(N-piperidino)phenyl)

17α-Acetoxy-19-norpregna-4,9-diene-3,20-dione (D-5, R=$CH_3$)

To a 0° C. suspension of p-toluene sulfonic acid (57 g, 0.302 mol), and acetic acid (216 mL, 3.78 mol) in 450 mL of $CH_2Cl_2$ was added slowly, in portions, 534 mL (3.78 mol) of trifluoroacetic anhydride while maintaining a temperature of 0° C. After a clear solution resulted, a cold (0° C.) solution of B-4 (50 g, 0.14 mol) in 300 mL of $CH_2Cl_2$ was added in one portion. The resulting yellow-brown solution was stirred at 0° C. for 10 min. The reaction mixture was poured over ice-water and basified with 2 L of saturated $K_2CO_3$ solution and additional solid $K_2CO_3$ to bring the pH to 9.0. The product was extracted with $CHCl_3$, dried over $Na_2SO_4$, filtered, evaporated, and dried to give 49.72 g (99% yield) of D-5, R=$CH_3$, as a light-yellow crystalline solid, used without further purification. $^1$H NMR (250 MHz; $CDCl_3$) δ 5.70 (bs, 1, 4-H), 2.12 (s, 3, 21-$CH_3$), 2.08 (s, 3, 17-OCOCH$_3$), 0.80 (s, 3, 18-$CH_3$).

17α-Acetoxy-3,3-[1,2-ethanediylbis(oxy)]-19-norpregna-5(10),9(11)-dien-20-one (D-6, R=$CH_3$)

A mixture of p-toluene sulfonic acid (1.33 g, 7.0 mmol), 115 mL (2.1 mol) of ethylene glycol, and 1.0 L of toluene was brought to reflux and 300 mL of toluene was distilled off. Compound D-5 (R=$CH_3$, 49.72 g, 0.14 mol) in 250 mL of toluene was added, the resulting mixture was heated to reflux and 300 mL of toluene was distilled. The reaction mixture was poured over ice-water and neutralized with saturated $NaHCO_3$ solution. The product was extracted with $CH_2Cl_2$, dried over $Na_2SO_4$, filtered, evaporated, and dried to afford 54 g of D-6, R=$CH_3$, used without further purification. $^1$H NMR (250 MHz; $CDCl_3$) δ 5.57 (bs, 1, 11-H), 3.99 (s, 4, 3-ketal), 2.07 (s, 3, 21-$CH_3$), 2.06 (s, 3, 17-OCOCH$_3$), 0.62 (s, 3, 18-$CH_3$).

17α-Acetoxy-3,3-[1,2-ethanediylbis(oxy)]-5(10)α-oxido-19-norpregn-9(11)-en-20-one (D-7, R=$CH_3$)

To a solution of ketal D-6 (R=$CH_3$, 25 g, 0.0625 mol) in 320 mL of methylene chloride cooled to 0° C. was added a cooled mixture (0° C.) of 14.7 mL (0.148 mol) of $H_2O_2$ (30%), 8.3 mL (0.059 mol) of hexafluoroacetone trihydrate, and 1.77 g (0.0125 mol) of $Na_2HPO_4$. The resulting mixture was stirred vigorously at 0° C. for 12 h. The cold reaction mixture was quenched with brine. The organic phase was extracted with $CH_2Cl_2$, dried with $MgSO_4$, filtered, and evaporated to a yellow solid (28.8 g) which was purified by SiO$_2$ flash column chromatography (EtOAc/hexane 1:1) to give 21.34 g of D-7, R=CH$_3$, accompanied by about 20% of the β-epoxide isomer (74% isolated yield from B-4). $^1$H NMR (250 MHz; CDCl$_3$) δ 6.05 (bs, 1, 11-H of the α-epoxide), 5.85 (bs, 0.2, 11-H of the β-epoxide), 3.92 (m, 4, 3-ketal), 2.08 (s, 3, 21-CH$_3$), 2.06 (s, 3, 17-OCOCH$_3$), 0.62 (s, 3, 18-CH$_3$).

17α-Acetoxy-3,3-[1,2-ethanediylbis(oxy)]-5α-hydroxy-11β-[4-(N-piperidino)phenyl]-19-norpregn-9-en-20-one (D-8, R=CH$_3$, Ar=4-(N-piperidino)phenyl)

A Grignard solution was freshly prepared from 55.47 g (0.23 mol) of 4-(N-piperidinyl)-phenyl bromide and 5.62 g (0.231 g-atom) of magnesium in 480 mL of THF in the presence of a catalytic amount (5 drops) of dibromoethane. To a stirred suspension of epoxide D-7 (R=CH$_3$, 24 g, 0.0577 mol) and CuI (21.9 g, 0.115 mol) in 480 mL of dry THF cooled to 0° C. under N$_2$ was added the Grignard reagent in one portion. After being stirred for 15 min, the greenish-yellow suspension was quenched with saturated NH$_4$Cl solution. The product was extracted with EtOAc and ether was added to facilitate the separation of the organic phase. The combined organic extracts were dried over Na$_2$SO$_4$, filtered and concentrated to give 65.10 g of crude reaction product which was purified by SiO$_2$ column chromatography (EtOAc/hexane 1:1) to give 27.71 g (93% yield) of D-8, R=CH$_3$. $^1$H NMR (250 MHz; CDCl$_3$) δ 7.02 (d, 2, J=8.6 Hz, aromatic-H), 6.8 (d, 2, J=8.6 Hz, aromatic-H), 4.44 (s, 1, 5-OH), 4.28 (d, 1, J=7.3 Hz, 11-H), 3.92 (m, 4, 3-ketal), 3.09 (m, 4, N—CH$_2$), 2.10 (s, 3, 21-CH$_3$), 2.06 (s, 3, 17-OCOCH$_3$), 0.27 (s, 3, 18-CH$_3$).

17α-Acetoxy-11β-[4-(N-piperidino)phenyl]-19-norpregna-4,9-diene-3,20-dione (D-4, R=CH$_3$, Ar=4-(N-piperidino)phenyl)

Trifluoroacetic acid (79 mL, 1.024 mol) was added dropwise to a mixture of D-8 (33.12 g, 0.064 mol) and H$_2$O (57 mL, 3.136 mol) in 2800 mL of CH$_2$Cl$_2$ at 0° C. The reaction mixture was stirred vigorously for 1.5 h and carefully neutralized with saturated NaHCO$_3$ solution (1.8 L). The product was extracted with CH$_2$Cl$_2$ and the combined extracts were dried over Na$_2$SO$_4$, filtered and concentrated to give 32.34 g of crude reaction product. Flash SiO$_2$ column chromatography (EtOAc/hexane 1:1) provided 9.47 g of pure D-4, R=CH$_3$, Ar=4-(N-piperidino)-phenyl. Recrystallization from EtOH gave 6.45 g of crystalline compound__ (>99% pure by HPLC, Reverse Phase YMC-C 18 Column, 85% MeOH: 15% H$_2$O, 1.0 mL/min). The less pure fractions (14.27 g) from the column chromatography was further purified by flash SiO$_2$ column chromatography (EtOAc/hexane 1:2) to afford 12.97 g of pure product which was recrystallized from EtOH to give another 9.76 g of crystalline product (>99% pure by HPLC). The crystalline compound contained ca. 1 mole of ethanol, as shown by NMR analysis. $^1$H NMR (250 MHz; CDCl$_3$) δ 6.90 (d, 2, J=8.7 Hz, aromatic-H), 6.82 (d, 2, J=8.7 Hz, aromatic-H), 5.78 (bs, 1, 4-H), 4.38 (d, 1, J=7.3 Hz, 11-H), 3.71 [m, 2, HOCH$_2$CH$_3$ (solvate)], 2.13 (s, 3, 21-CH$_3$), 2.09 (s, 3, 17-OCOCH$_3$), 1.23 [t, 3, HOCH$_2$CH$_3$ (solvate)], 0.34 (s, 3, 18-CH$_3$).

EXAMPLE 5

Synthesis of 11β-[4-(N,N-dimethylamino)phenyl]-17α-propionyloxy-19-norpregna-4,9-diene-3,10-dione (D-4, Ar=Me$_2$N—CH$_6$H$_4$—, R=CH$_2$CH$_3$ A solution of propionic acid (1.70 g, 22.9 mmol) and p-TsOH (1.45 g, 7.65 mmol) in 10 mL of CH$_2$Cl$_2$ was cooled to 0° C. Trifluoroacetic anhydride (9.64 g, 45.9 mmol) was added to the cooled solution followed by a solution of 400 mg (0.765 mmol) of D-3 (Ar=Me$_2$N—C$_6$H$_4$—, WO 89/12448 and WO 96/30390) in 5 mL of CH$_2$Cl$_2$. Water was added to the mixture after stirring for 1 h at 0° C. Saturated NaHCO$_3$ solution was added and the mixture adjusted to pH>8 by the addition of solid K$_2$CO$_3$. The organic phase was separated and the aqueous phase extracted with CH$_2$Cl$_2$. The organic solutions were combined washed with brine and dried (MgSO$_4$). Evaporation of the solvent gave the crude product which was purified by column chromatography on silica gel to give 175 mg (47% yield) of D-4 (Ar=Me$_2$N—C$_6$H$_4$—, R=CH$_2$CH$_3$); $^1$H NMR (250 MHz; CDCl$_3$) δ 6.98 (d, 2, Ar—H), 6.63 (d, 2, Ar—H), 5.77 (s, 1, 4-H), 4.38 (bd, 1, 11-H), 2.91 [s, 6, N(CH$_3$)$_2$], 2.09 (s, 3, 21-CH$_3$), 1.18 (t, 3, CH$_3$CH$_2$COO), 0.36 (s, 3, 18-CH$_3$); mass spectrum, m/z 489 (M$^+$), 400, 372, 251, 121. Anal. Calcd for C$_{31}$H$_{39}$NO$_4$.0.5 H$_2$O: C, 74.67; H, 8.08; N, 2.81. Found: C, 74.74; H, 7.92; N, 2.54.

The following examples were prepared by the method described above by reaction of the appropriate D-3 with the corresponding carboxylic acid in the presence of trifluoroacetic anhydride and p-toluenesulfonic acid.

EXAMPLE 6

11β-[4-(N,N-Dimethylamino)phenyl]-17α-phenylacetoxy-19-norpregna-4,9-diene-3,20-dione $^1$H NMR (250 MHz; CDCl$_3$) δ 7.35 (m, 5, C$_6$H$_5$CH$_2$COO), 6.95 (d, 2, Ar—H), 6.62 (d, 2, Ar—H), 5.79 (s, 1, 4-H), 4.32 (bd, 1, 11-H), 4.24 (m, 2, C$_6$H$_5$CH$_2$COO), 2,90 [s, 6, N(CH$_3$)$_2$], 2.02 (s, 3, 21-CH$_3$), 0.32 (s, 3, 18-CH$_3$); mass spectrum, m/z 551 (M$^+$), 417, 372, 251, 121. Anal. Calcd for C$_{36}$H$_{41}$NO$_4$: C, 78.37; H, 7.49; N, 2.54. Found: C, 78.25; H, 7.49; N, 2.52.

EXAMPLE 7

11β-[4-(N,N-Dimethylamino)phenyl]-17α-benzoyloxy-19-norpregna-4,9-diene-3,20-dione $^1$H NMR (250 MHz; CDCl$_3$) δ 8.04 (m, 2, Ar—H), 7.44–7.64 (m, 3, Ar—H), 6.99 (d, 2, Ar—H), 6.64 (d, 2, Ar—H), 5.78 (s, 1, 4-H) 4.47 (bd, 1, 1 1-H) 2.96 [s, 6, N(CH$_3$)$_2$], 2.12 (s, 3, 21-CH$_3$) 0.42 (s, 3, 18-CH$_3$). mass spectrum, m/z 537 (M$^+$), 417, 372, 251, 121. Anal. Calcd for C$_{36}$H$_{39}$NO$_4$.0.5 H$_2$O: C, 76.89; H, 7.37; N, 2.56. Found: C, 76.92; H, 7.26; N, 2.54.

Other propionate esters were prepared from D5 (R=—CH$_2$CH$_3$, prepared by a method analogous to that described for preparing D-5, R=—CH$_3$) by ketalization with ethylene glycol and p-toluenesulfonic acid to give D-6 (R=—CH$_2$CH$_3$) followed by epoxidation with hydrogen peroxide and hexafluoroacetone to give epoxide D-7 (R=—CH$_2$CH$_3$). The copper(1) catalyzed reaction of the appropriate Grignard reagent with D-7 (R=—CH$_2$CH$_3$) followed by acid catalyzed hydrolysis of the resulting D-8 (R=—CH$_2$CH$_3$) gave the following D-4 (R=—CH$_2$CH$_3$).

EXAMPLE 8

17α-Propionyloxy-11β-[4-(N-pyrrolidino)phenyl-19-norpregna-4,9-diene-3-20-dione $^1$H NMR (250 MHz; CDCl$_3$) δ 6.96 (d, 2, Ar—H), 6.45 (d, 2, Ar—H), 5.77 (s, 1, 4-H), 4.38 (bd, 1, 11-H), 2.08, (s, 3, 21-CH$_3$), 1.21 (t, 3, CH$_3$CH$_2$COO), 0.38 (s, 3, 18-CH$_3$); mass spectrum, m/z 515 (M$^+$), 446, 354, 147. Anal. Calcd for C$_{33}$H$_{41}$NO$_4$.0.25.H$_2$O: C, 76.19; H, 8.04; N, 2.67. Found: C, 76.05; H, 8.05; N, 2.67.

EXAMPLE 9

11β-(1-Methylindol-5-yl)-17α-propionyloxy-19-norpregna-4,9-diene-3,20-dione $^1$H NMR (250 MHz; CDCl$_3$) δ 7.26 (m, 3, Ar—H), 7.03 (m, 1, Ar—H) 6.38 (d, 1, J=3 Hz, Ar—H), 5.80 (s, 1, 4-H), 4.58 (bd, 1, 11-H), 3.76 (s, 3, NCH$_3$), 2.08 (s, 3, 21-CH$_3$), 1.19 (t, 3, CH$_3$CH$_2$COO), 0.34 (s, 3, 18-CH$_3$); mass spectrum, m/z 499 (M$^+$), 425, 382, 251, 131. Anal. Calcd for C$_{32}$H$_{37}$NO$_4$.0.25 H$_2$O: C, 76.24; H, 7.50; N, 2.78. Found: C, 76.05; H, 7.53; N, 2.61.

EXAMPLE 10

Synthesis of 17α-Acetoxy-11β-(1-methyl-2,3-dihydroindol-5-yl)-19-norpregna-4,9-diene-3,20-dione SiOO$_2$ column chromatography (EtOAc/hexane 1:1) provided 9.47 g of pure D-4, R=CH$_3$, Ar (D-4, Ar=1-methyl-2,3-dihydroindol-5-yl R=CH$_3$)

3,20-Bis[3,3-ethandilybis(oxy)]-5α-hydroxy-11β-(1-methyl-2,3-dihydroindol-5-yl)-19-norpregn-9-en-17α-ol (D-3, Ar=1-methyl-2,3-dihydroindol-5-yl)

Copper(1) bromide-dimethyl sulfide complex was added to a Grignard reagent freshly prepared from 1.32 g (6.22 mmol) of 5-bromo-1-methyl-2,3-dihydroindol and 181 mg (7.46 mmol) of magnesium in 10 mL of dry THF. The solution was stirred for 30 min and then was cooled to 0° C. A solution of 518 mg (1.24 mmol) of D-2 (WO 96/30390) in 5 mL of THF was added. The mixture was slowly warmed to ambient temperature and stirred for 1 h. The reaction was quenched with aqueous NH$_4$Cl and extracted with CH$_2$Cl$_2$. The CH$_2$Cl$_2$ solution was washed with brine and dried (MgSO$_4$). Evaporation of the solvent afforded the crude product which was purified by chromatography on silica gel (CH$_2$Cl$_2$/acetone 100:5) to give 200 mg (30% yield) of D-3 (Ar=1-methyl-2,3-dihydroindol-5-yl). $^1$H NMR (250 MHz; CDCl$_3$) δ 6.95 (s, 1, Ar—H), 6.85 (d, 1, Ar—H), 6.35 (d, 1, Ar—H), 3.9 (m, 8, 3- and 20-ketal), 2.71 (s, 3, N—CH$_3$), 1.39 (s, 3, 21-CH$_3$), 0.48 (s, 3, 18-CH$_3$).

17α-Acetoxy-11β-(1-methyl-2,3-dihydroindol-5-yl)-19-norpregna-4,9-diene-3,20-dione (D-4, Ar=1-methyl-2,3-dihydroindol-5-yl, R=CH$_3$)

A solution of AcOH (612 mg, 10.2 mmol) and p-TsOH (646 mg, 3.4 mmol) in 8 mL of CH$_2$Cl$_2$ was cooled to 0° C. Trifluoroacetic anhydride (4.24 g, 20.2 mmol) was added to the cooled solution followed by a solution of 180 mg (0.34 mmol) of D-3 (Ar=1-methyl-2,3-dihydroindol-5-yl) in 5 mL of CH$_2$Cl$_2$. Water was added to the mixture after stirring for 1 h at 0° C. Saturated NaHCO$_3$ solution was added, and the mixture adjusted to pH >8 by the addition of solid K$_2$CO$_3$. The organic phase was separated and the aqueous phase extracted with CH$_2$Cl$_2$. The organic solutions were combined washed with brine and dried (MgSO$_4$). Evaporation of the solvent gave the crude product which was purified by column chromatography on silica gel (CH$_2$Cl$_2$/acetone 100:5) and crystallization from ether/hexane to give 47 mg (28% yield) of D-4 (Ar=1-methyl-2,3-dihydroindol-5-yl, R=CH$_3$). $^1$H NMR (250 MHz; CDCl$_3$) δ 6.84 (s, 1, Ar—H), 6.78 (d, 1, Ar—H), 6.34 (d, 1, Ar—H), 5.78 (s, 1, 4-H), 4.35 (m, 1, 11-H), 2.93 (s, 3, N—CH$_3$), 2.13 (s, 3, CH$_3$CO), 2.10 (s, 3, CH$_3$CO), 0.38 (s, 3, 18-CH$_3$).

The following D-4 were prepared in a similar manner by reaction of the appropriate Grignard reagent with D-2 followed by reaction of the resulting D-3 with AcOH in the presence of trifluoroacetic anhydride and p-toluenesulfonic acid.

EXAMPLE 11

17α-Acetoxy-11β-(4-methoxyphenyl)-19-norpregna-4,9-diene-3,20-dione $^1$H NMR (250 MHz; CDCl$_3$) δ 7.04 (d, 2, Ar—H), 6.80 (d, 2, Ar—H), 5.79 (s, 1, 4-H), 4.41 (bd, 1, 11-H), 3.77 (s, 3, OCH$_3$), 2.13 (s, 3, CH$_3$CO), 2.09 (s, 3, CH$_3$CO), 0.33 (s, 3, 18-CH$_3$); mass spectrum, m/z 462 (M$^+$), 402, 359, 331, 251.

EXAMPLE 12

17α-Acetoxy-11β-[4-(N-pyrrolidino)phenyl]-19-norpregna-4,9-diene-3-20-dione $^1$H NMR (250 MHz; CDCl$_3$) δ 6.95 (d, 2, Ar—H), 5.46 (d, 2, Ar—H), 5.77 (s, 1, 4-H), 4.38 (bd, 1, 11-H), 2.13, (s, 3, CH$_3$CO), 2.10 (s, 3, CH$_3$CO), 0.38 (s, 3, 18-CH$_3$); mass spectrum, m/z 501 (M$^+$), 147. Anal. Calcd for C$_{32}$H$_{39}$NO$_4$.0.75 H$_2$O: C, 74.60; H, 7.92; N, 2.72. Found: C, 74.49; H, 7.81; N, 2.69.

EXAMPLE 13

17α-Acetoxy-11β-(1-methylindol-5-yl)-19-norpregna-4,9-diene-3,20-dione $^1$H NMR (250 MHz; CDCl$_3$) δ 7.23 (m, 3, Ar—H), 7.01 (d, 1, Ar—H) 5.79 (s, 1, 4-H), 4.58 (bd, 1, 11-H), 3.75 (s, 3, N—CH$_3$), 2.14 (s, 3, CH$_3$CO), 2.08 (s, 3, CH$_3$CO), 0.32 (s, 3, 18-CH$_3$); mass spectrum, m/z 485 (M$^+$), 425, 382, 251. Anal. Calcd for C$_{31}$H$_{35}$NO$_4$: C, 76.67; H, 7.27; N, 2.88. Found: C, 75.99; H, 7.30; N, 2.81.

EXAMPLE 14

17α-Acetoxy-11β-(4-N,N-Dimethylamino-3-fluorophenyl)-19-norpregna4,9-diene-3,20-dione SiOO$_2$ column chromatography (EtOAc/hexane 1:1) provided 9.47 g of pure D-4, R =CH$_3$, Ar $^1$H NMR (250 MHz; CDCl$_3$) δ 6.75 (m, 3, Ar—H), 5.79 (s, 1, 4-H), 4.37 (bd, 1, 11-H), 2.88 [s, 6, N(CH$_3$)$_2$], 2.13 (s, 3, CH$_3$CO), 2.11 (s, 3, CH$_3$CO), 0.35 (s, 3, 18-CH$_3$); mass spectrum, m/z 493 (M$^+$), 433, 390, 251, 139. Anal. Calcd for C$_{30}$H$_{36}$FNO$_4$: C, 73.00; H, 7.35; N, 2.84. Found: C, 72.88; H, 7.42; N, 2.88.

EXAMPLE 15

17α-Acetoxy-11β-[2-(N,N-dimethylamino)pyrid-5-yl]-19-norpregna-4,9-diene-3,20-dione $^1$H NMR (250 MHz; CDCl$_3$) δ 7.89 (d, 1, J=2.5 Hz, Pyr-H), 6.27 (dd, 1, J=2.5,10 Hz, Pyr-H), 6.47 (d, 1, J=10 Hz, Pyr-H), 5.77 (s, 1, 4-H), 4.35 (bd, 1, 11-H), 3.05 [s, 6, N(CH$_3$)$_2$], 2.13 (s, 3, CH$_3$CO), 2.09 (s, 3, CH$_3$CO), 0.41 (s, 3, 18-CH$_3$); mass spectrum, m/z 476 (M$^+$), 416, 373, 251, 122. Anal. Calcd for C$_{29}$H$_{36}$N$_2$O$_4$: C, 73,08; H, 7.61; N, 5.88. Found: C, 72.54; H, 7.62; N, 5.85.

EXAMPLE 16

Synthesis of 11β-[4-(N,N-dimethylamino)phenyl]-17α-ethyl-19-norpregna-4,9-diene-3,20-dione (E-8, Ar=4-Me$_2$N—C$_6$H$_4$—, R=—CH$_2$CH$_3$)

17-Cyano-3,3-[ethandiylbis(oxy)]estra-5(10),9(11)-diene (E- 1)

A solution of B-1 (6.0 g, 19.1 mmol) in 200 mL of dry THF was added to a 0.5 M solution of LiCN (115 mL, 57.3 mmol) in DMF, followed by addition of 9.34 g (57.3 mmol) of diethyl cyanophosphonate. The mixture was stirred for 30 min at ambient temperature before dilution with water and extraction with EtOAc/hexanes (1:1) three times. The organic solution was washed with brine and dried ($MgSO_4$). Removal of the solvent gave the crude phosphate as a thick oil.

Samarium(11) iodide solution (0.1 M in THF, 764 mL, 76.4 mmol) was transferred under $N_2$ to a flask. A solution of the crude product from above in 240 mL of THF and 2.83 g (38.2 mmol) of t-BuOH was added and the reaction mixture was stirred overnight. The reaction was quenched with $NH_4Cl$ solution and extracted with EtOAc/hexanes (1:1). The organic phase was washed with brine and dried ($MgSO_4$). Removal of the solvent gave a crude product which was purified by flash chromatography on silica gel. Yield 4,92 g (79%) of E-1 as a mixture of 17α- and 17β-isomers. $^1H$ NMR (250 MHz; $CDCl_3$) δ 5.56 (m, 1, 11-H), 3.99 (bs, 4, 3-ketal), 0.91 and 0.82 [s, 3 (total for both signals), 18-$CH_3$ of the α-__ and β-isomers].

17β-Cyano-3,3-[ethandiyl(oxy)]-17α-ethylestra-5(10),9(11)-diene (E-2, R=—$CH_2CH_3$)

A solution of $Et_2NH$ (0.898 g, 12.3 mmol) in 20 mL of dry THF was cooled to −78° C. and 3.69 mL of n-BuLi solution ( 2.5 M in hexane, 9.25 mmol) was added. The mixture was stirred at −78° C. for 20 min. In a separate flask, 2.0 g of E-1 was dissolved in 40 mL of dry THF. This solution was cooled to −78° C. and the $Et_2NLi$ solution added to it. After stirring for 20 min at −78° C., ethyl iodide (4.03 g, 25.8 mmol) was added to the bright orange solution. The mixture was stirred at −78° C. for 30 min and at ambient temperature for 20 min. Saturated $NH_4Cl$ solution was added and the mixture was extracted with EtOAc. The organic solution was washed with brine and dried ($MgSO_4$). Evaporation of the solvent provided the crude product which was purified by flash chromatography on silica gel using EtOAc/hexanes (1:4) as eluant to afford 1.63 g (75% yield) of E-2 (R=—$CH_2CH_3$). $^1H$ NMR (250 MHz; $CDCl_3$) δ 5.58 (bs, 1, 11-H), 3.99 (bs, 4, 3-ketal), 1.15 (t, 3, —$CH_2CH_3$), 1.06 (s, 3, 18-$CH_3$).

3,3-[Ethandiylbis(oxy)]-17β-ethyl-17β-formylestra-5(10),9(11)-diene (E-3, R=—$CH_2CH_3$)

A solution of DIBAL-H (17.6 mL, 1.0 M in toluene, 17.6 mmol) was added dropwise to a solution of 3.1 g (8.78 mmol) of E-2 (R=$CH_2CH_3$) in 400 mL of freshly distilled toluene at −42° C. (acetonitrile-Dry-ice bath). After the addition was complete, the mixture was stirred at −42° C. for 1 h. Saturated $NH_4Cl$ solution was added and the mixture allowed to warm to ambient temperature. The mixture was stirred at ambient temperature overnight. The organic phase was separated and the aqueous phase was extracted twice with toluene. The combined organic phase was washed with brine and dried ($MgSO_4$). Evaporation of the solvents gave the crude product which was purified by flash chromatography on silica gel (EtOAc/hexanes 1:4) to give 2.3 g (73% yield) of E-3 (R=—$CH_2CH_3$). $^1H$ NMR (250 MHz; $CDCl_3$) δ 9.54 (s, 1, —CHO), 5.57 (bs, 1, 11-H), 3.98 (bs, 4, 3-ketal), 0.74 (t, $CH_2CH_3$), 0.71 (s, 18-$CH_3$).

3,3-[Ethandiylbis(oxy)]-17β-ethyl-20-hydroxy-19-norpregna-5(10),9(11)-diene (E-4, R=—$CH_2CH_3$)

Methyllithium (9.3 mL, 1.4 M in THF, 12.9 mmol) added to a solution of E-3 (R=$CH_2CH_3$) (2.3 g, 6.5 mmol) in 230 mL of dry THF at −78° C. The mixture was stirred at −78° C. for 30 min and then allowed to slowly warm to room temperature. After stirring for an additional 10 min, saturated $NH_4Cl$ solution was added. The resulting mixture was extracted with EtOAc, and the combined EtOAc washes back washed with brine and dried ($MgSO_4$). Removal of the solvent afforded 2.28 g (95% yield) of product suitable for the next reaction. $^1H$ NMR (250 MHz; $CDCl_3$) δ 5.49 (s, 1, 11-H), 3.91 (s, 4, 3-ketal), 1.06 (d, 3, 21-$CH_3$), 0.90 (t, 3, $CH_2CH_3$), 0.78 (s, 3 18-$CH_3$).

3,3-[Ethandiylbis(oxy)]-17α-ethyl-19-norpregna-5(10),9(11)-dien-20-one (E-5, R=—$CH_2CH_3$)

A solution of DMSO (503 mg, 6.45 mmol) in 1 mL of $CH_2Cl_2$ was added to a solution of oxalyl chloride (375 mg, 2.96 mmol) in 5 mL of $CH_2Cl_2$ at −60° C. (Dry-ice/$CHCl_3$ bath). The mixture was stirred at −60° C. for 10 min. A solution of E-4 (R=$CH_2CH_3$) (500 mg, 1.34 mmol) in 2 mL of $CH_2Cl_2$ was added. The mixture was stirred for 15 min at −60° C. TEA (1.49 g, 14.8 mmol) was added and the mixture was allowed to warm to ambient temperature. The reaction was quenched with water and extracted with $CH_2Cl_2$. The $CH_2Cl_2$ extract was washed with water, then brine and dried ($MgSO_4$). The crude product was purified by chromatography on silica gel ($CH_2Cl_2$/acetone 100:1) to afford 354 mg (71% yield) of E-5 (R=—$CH_2CH_3$). $^1H$ NMR (250 MHz; $CDCl_3$) δ 5.23 (m, 1, 11-H), 3.95 (s, 4, 3-ketal), 2.02 (s, 3, 21-$CH_3$), 0.73 (t, 3, $CH_2CH_3$), 0.71 (s, 3, 18-$CH_3$).

3,3-[Ethandiylbis(oxy)]-17α-ethyl-5(10)α-oxido-19-norpregn-9(11)-en-20-one ( E-6, R=—$CH_2CH_3$)

Hexafluoroacetone trihydrate (73 μL) and 2.8 mL of 0.1 M $Na_2HPO_4$ solution were added to a solution of 335 mg (0.91 mmol) of E-5 (R=—$CH_2CH_3$) in 2 mL of $CH_2Cl_2$. The solution was cooled to 0° C. before adding 89 μL of 50% hydrogen peroxide solution. The mixture was slowly warmed to ambient temperature and stirred overnight. The reaction was quenched with 10% aqueous $Na_2S_2O_3$ solution and extracted with $CH_2Cl_2$. The $CH_2Cl_2$ extract was washed with water, then brine and dried ($MgSO_4$). The crude product was purified by flash chromatography on silica gel ($CH_2Cl_2$/acetone 100:3) to give 150 mg (43% yield) of E-6 (R=—$CH_2CH_3$).

11β-4-(N,N-Dimethylamino)phenyl]-3,3-[ethandiylbis(oxy)]-17α-ethyl-5β-hydroxy-19-norpregn-9-en-20-one (E-7, Ar=4-$Me_2N$—$C_6H_4$—, R=—$CH_2CH_3$)

Copper(1) bromide-dimethyl sulfide complex (800 mg, 3.9 mmol) was added to 3.9 mL (3.9 mmol) of a 1 M solution of 4-(N,N-dimethylamino)phenylmagesium bromide in THF. The mixture was stirred at ambient temperature for 30 min. A solution of 150 mg (0.39 mmol) of E-6 (R=—$CH_2CH_3$) in 2 mL of dry THF was added and the reaction was stirred at ambient temperature for 2 days. The mixture was quenched with aqueous $NH_4Cl$ solution and extracted with $CH_2Cl_2$. The $CH_2Cl_2$ solution was washed with brine and dried ($MgSO_4$). The crude product was purified by flash chromatography on silica gel ($CH_2Cl_2$/acetone 100:3) to give 130 mg (66% yield) of E-7 (Ar=4-$Me_2N$—$C_6H_4$—, R=—$CH_2CH_3$). $^1H$ NMR (250 MHz; $CDCl_3$) δ 7.03 (d, 2, Ar—H), 6.63 (d, 2, Ar—H), 4.25 (m, 1, 11-H), 3.96 (m, 4, 3-ketal) 2.90 (s, 6, $N(CH_3)_2$), 2.03 (s, 3, 21-$CH_3$), 0.71 (t, 3, —$CH_2CH_3$), 0.28 (s, 3, 18-$CH_3$).

11β-[4-(N,N-Dimethylamino)phenyl]-17α-ethyl-19-norpregna-4,9-dien-3,20-dione (E-8, Ar=4-$Me_2N$—$CH_6H_4$—, R=—$CH_2CH_3$)

Two drops of concentrated HCl were added to a solution of 130 mg (0.26 mmol) of E-7 (R=—$CH_2CH_3$) in 10 mL of methanol. The mixture was stirred at ambient temperature for 2 h. The solvent was evaporated and the residue was treated with aqueous $NaHCO_3$ solution and extracted with $CH_2Cl_2$. The $CH_2Cl_2$ was washed with brine and dried ($MgSO_4$). Evaporation of the solvent provided the crude product which was purified by chromatography on silica gel ($CH_2Cl_2$/acetone 100:3) to afford 70 mg (61% yield) of E-8

(R=—CH$_2$CH$_3$). $^1$H NMR (250 MHz; CDCl$_3$) δ 6.94 (d, 2, Ar—H), 6.57 (d, 2, Ar—H), 5.69 (s, 1, 4-H), 2.84 [s, 6, N(CH$_3$)$_2$], 2.03 (s, 3, 21-CH$_3$), 0.67 (t, 3, —CH$_2$CH$_3$), 0.28 (s, 3, 18-CH$_3$).

The biological activity of the compounds of this invention was examined by means of in vitro and in vivo tests.

Receptor Binding

The affinity of the compounds for the progesterone hormone receptor was determined by standard procedures similar to those that have been described in C. E. Cook, et al., Human Reproduction, Volume 9, supplement 1, pp. 32–39 (1994). However, the receptors were of human origin and a different radioligand was used. Thus, for progestin receptor binding the receptor was obtained in cytosol from human T-47D breast cells and [$^3$H]-R5020 was used as the radioligand. Data are expressed as IC$_{50}$ values, i.e., the concentration of compound that inhibits the radioligand binding by 50%.

Table 1 shows that compounds of the present invention bind strongly to the progestin receptor but with varying degrees of affinity. Cellular and whole animal tests were also performed to further characterize the biological activity of the compounds of the invention.

Determination of progestational and antiprogestational activity in human cells

Human T-47D breast cells grown in nutrient media were incubated with the standard progestin R5020 alone or with R5020 plus test compound and then assessed by standard procedures for proliferation using incorporation of [$^3$H]-thymidine as the measurement. Table 2 shows results of these assays. Data for antiprogestin activity are expressed as EC$_{50}$, i.e., the concentration of compound which inhibits 0.15 nM R5020-mediated proliferation by 50%. The maximum % inhibition (a measure of the efficacy of the compounds) is also given. In the agonist format of this assay the compounds were tested at concentrations ranging from 0.01 to 10 nM and the maximum % stimulation at any dose is listed in Table 2. It can be seen that for the most part the compounds lack progestational activity and exhibit potent antiprogestational activity in this assay. However, the presence of a very polar hydroxyl group in the 17α-position greatly diminishes antiprogestational activity and this holds even when the OH is separated from the 17-carbon atom by a methylene group.

Determination of progestational and antiprogestational activity in vivo

Progestational activity and antiprogestational activity were determined in rabbits by means of the McGinty test (test compound alone, procedure of McGinty et al., Endocrinology, 24:829–832 (1939)) or anti-McGinty test (test compound plus progesterone, procedure of Tamara et al., Jpn. J. Fertil. Steril. 24:48–81 (1979)). Results were scored according to McPhail (McPhail, J. Physiol., 83:146 (1934)). These are standard procedures well-known to those skilled in the art. The results of these assays are shown in Table 3 (agonist activity) and 4 (antagonist activity). Here it was found that surprisingly, in this classical test of progestational and antiprogestational activity, some of the compounds exhibited either agonist or mixed agonist/antagonist activity. Although Cook et al. (Human Reproduction, Volume 9, Supplement 1, pp. 32–39 (1994)) have reported that 16α-ethyl substitution can reverse the profile of certain 11β-aryl-19-norpregnane steroids from antagonist to agonist, it has not been previously reported that such reversal can be effected by substituent variation at the 17α-position. But as shown in Table 3, substitution of a 17α-methoxymethyl group can result in significant progestational activity. Even more surprisingly, it was found that variations at the 4-position of the 11β-aryl group can have this effect. In a comprehensive summary of antiprogestational compound activities, Teutsch (Human Reproduction, Volume 9, Supplement 1, pp. 12–31 (1994)) makes no mention of this phenomenon. However, comparison of 17α-acetoxy-11β-(4-(N,N-dimethylamino)phenyl)-19-norpregna-4,9-diene-3,20-dione (Cook et al, Human Reproduction, Volume 9, Supplement 1, pp. 32–39 (1994)) with 17α-acetoxy-11β(-4-methoxyphenyl)-19-norpregna-4, 9-diene-3,20-dione (Tables 3 and 4) shows the former compound to have potent antiprogestational activity, whereas the latter has both agonist and antagonist properties in this assay. It appears that the presence of a basic nitrogen substituent at the 4-position of the aryl group in this series is necessary for potent antiprogestational activity as defined by this widely accepted assay. Thus, it may be observed that the presence of a strongly electron-withdrawn fluorine atom in the 3-position of a 4-dimethylamino aryl substituent, which lowers the basicity of the adjacent amino group, results in strong progestational activity, with little or no observed antiprogestational activity.

Furthermore incorporation of the nitrogen into a cyclic structure, either monocyclic or bicyclic, surprisingly retains the potent antiprogestational activity. Thus 17α-acetoxy-11β-(4-(N-piperidino)phenyl)-19-norpregna-4,9-diene-3, 20-dione was subjected to the anti-Clauberg assay (McPhail, J. Physiol., 83:146 (1934)) for oral antiprogestational activity. In this assay immature New Zealand white rabbits were primed with estrogen by treatment with estradiol for six days. They were then given progesterone subcutaneously (SC) and the test compound (orally) for 5 days. On the day following the treatment, the uteri were excised and examined histologically. The endometrial response was graded by the method of McPhail and the % inhibition was determined at each dose. Statistical analysis provides for an ED$_{50}$ value. For this compound the ED50 was 0.9 mg/day compared with an ED50 of 4.14 mg/day for the known antiprogestin mifepristone. In addition, the compound of this invention was 100% effective in inhibiting the endometrial response, whereas mifepristone was only 67% effective. Therefore, the test compound was about 5 fold more potent than mifepristone in this assay and the inhibition was more complete than that produced by mifepristone.

Reversal of the 17α-O—CO—CH$_3$ to the 17α-CO—OCH$_3$ results in a highly potent antiprogestational compound without any significant progestational activity. Linking the 17β-acetyl and 17α-acetoxy moieties to form a spiro-ketolactone (structure II) also results in potent antiprogestational activity with no evidence of progestational activity. Furthermore, when this latter compound was studied for its ability to bind to the androgen receptor (using the cytosolic receptor from rat central prostate and [$^3$H]-5α-dihydrotestosterone as the radioligand), it was found to have very low affinity (IC$_{50}$ of 90 nM vs. 0.2 nM for R1881).

Antiglucocorticoid Activity in vivo

The ability of the compounds to block the effects of dexamethasone (6 μg per day for 7 days) on thymus weight of immature male rats was assessed. Certain of the compounds showed no antiglucocorticoid activity at a dose of 1000 μg per day. Thus control animals had thymus weights averaging 307±17 (S.E.) mg; animals treated with 6 μg of dexamethasone alone had thymus weights averaging 65±8 mg; and animals treated with 6 μg of dexamethasone and 1,000 μg of 17α-acetoxy-11β-(1-methylindol-5yl)-19-norpregna-4,9-diene-3,20-dione had thymus weights averaging 105±8 mg, not significantly different from dexamethasone alone, showing that the compound had little or no antiglucocorticoid activity in vivo. Neither did it show significantglucocorticoid activity when given alone (thymus weight 270±13 mg).

Anti-estrogenic Activity

The compounds were not anti-estrogenic when tested in vitro in the Ishikawa human endometrial adenocarcinoma cell line for ability to block estrogen-stimulated alkaline phosphates activity (for methods see for example Holinka, et al. (Cancer Res, 46:2771–2774 (1986) and Simard (Cancer Res. 57:3494–3497 (1997)). In addition, the compounds displayed little affinity for the human estrogen receptor ($IC_{50}$>3,000 nM) compared to mifepristone ($IC_{50}$=783 nM). However, in vivo they exhibited non-competitive anti-estrogenic activity of the type reported for mifepristone, for example by Wolf et al. (Fertil. Steril. 52: 1055–1060 (1989). Surprisingly they exhibited this activity in spite of the fact that they do not have the 17β-hydroxyl substituent characteristic of both mifepristone and estrogens such as estradiol but instead have the 17β-acetyl substituent characteristic of progesterone. Thus, 17α-acetoxy- 11β-(4-(N-piperidino) phenyl)-19-norpregna-4,9-diene-3,20-dione was inactive in the Ishikawa assay at concentrations up to $10^{-6}$ M. However, when immature female rabbits were administered that compound orally at 10 mg/day concurrently with 5 μg of estradiol per day and the uteri were removed and weighed, the uterine weight, was reduced compared to estrogen treated rabbits. The weight of uteri from untreated immature rabbits was increased from 246±87 (S.E.) mg with no estradiol to 1402±104 mg with estradiol alone. Concurrent treatment of rabbits with estradiol and 10 mg/day of 17α-acetoxy-11β-(4-(N-piperidino)phenyl)-19-norpregna-4,9-diene-3,20-dione reduced the uterine weights to 998±98 mg. Likewise 17α-acetoxy-11β-(4-N-pyrrolidino)phenyl)-19-norpregna-4,9-diene-3,20-dione at 10 mg/day reduced the uterine weight to 919±115 mg, and 17α-acetoxy-11β-(1-methyl-5-indolyl)-19-norpregna-4,9-diene-3,20-dione reduced uterine weight to 956±115 mg at the same dose. The latter compounds were also inactive in the Ishikawa cell assay for anti-estrogenic activity.

Within the context of the present invention, treatment of the activity of progesterone comprises both agonist and antagonist activity.

TABLE 1

Receptor Binding Affinity

| Structure | $R^1$ | $R^{12}$ | X | $R^6$ | $R^7$ | $R^9$ | $R^{10}$ | $R^{11}$ | Relative Binding Affinity hPR $IC_{50}$ (nM) |
|---|---|---|---|---|---|---|---|---|---|
| Progesterone | | | | | | | | | 3.3 |
| I | 4-Me$_2$N | H | O | H | C$_2$H$_5$ | H | — | — | 0.6 |
| I | 1-methyl-2,3-dihydroindol-5-yl | O | H | —O—CO—CH$_3$ | H | — | — | 2.0 |
| I | 4-(N-piperidino) | H | O | H | —O—CO—CH$_3$ | H | — | — | 1.2 |
| I | 4-CH$_3$O | H | O | H | —O—CO—CH$_3$ | H | — | — | 0.8 |
| I | 4-Me$_2$N | H | O | H | —O—CO—C$_2$H$_5$ | H | — | — | 1.3 |
| I | 4-(N-pyrrolidino) | H | O | H | —O—CO—CH$_3$ | H | — | — | 0.8 |
| I | 4-Me$_2$N | H | O | H | O—CO—CH$_2$C$_6$H$_5$ | H | — | — | 7.9 |
| I | 4-Me$_2$N | H | O | H | —OH | H | — | — | 26.0 |
| I | 4-Me$_2$N | H | O | H | —O—CO—C$_6$H$_5$ | H | — | — | 24.0 |
| I | 1-methylindol-5-yl | O | H | —O—CO—CH$_3$ | H | — | — | 2.4 |
| I | 4-Me$_2$N | H | 3-F | O | H | —O—CO—CH$_3$ | H | — | — | 2.2 |
| I | 2-dimethylamino-5-pyridyl | O | H | —O—CO—CH$_3$ | H | — | — | 11.0 |
| I | 4-Me$_2$N | H | O | H | —CCH | H | — | — | 2.5 |
| I | 4-Me$_2$N | H | O | H | CH$_2$—O—CO—CH$_3$ | H | — | — | 10.6 |
| I | 4-Me$_2$N | H | O | H | —CH$_2$—OH | H | — | — | 43.6 |
| I | 4-Me$_2$N | H | O | H | —CH$_2$OCH$_3$ | H | — | — | 3.2 |
| I | 4-(N-piperidino) | H | O | H | —O—CO—C$_2$H$_5$ | H | — | — | 2.0 |
| I | 4-(N-pyrrolidino) | H | O | H | —O—CO—C$_2$H$_5$ | H | — | — | 4.8 |
| I | 1-methylindol-5-yl | O | H | —O—CO—C$_2$H$_5$ | H | — | — | 2.3 |
| I | 4-Me$_2$N | H | O | H | COOCH$_3$ | H | — | — | 0.7 |
| II | 4-Me$_2$N | H | O | H | — | H | H | H | 11.9 |

TABLE 2

T47D Cell Activity

| Structure | $R^1$ | $R^{12}$ | X | $R^6$ | $R^7$ | $R^9$ | $R^{10}$ | $R^{11}$ | Antagonist EC50 (nm) | Cell Proliferation % Inhib. | Agonist % Stim. |
|---|---|---|---|---|---|---|---|---|---|---|---|
| I | 4-Me$_2$N | H | O | H | C$_2$H$_5$ | H | — | — | 0.3 | 110 | 8 |
| I | 1-methyl-2,3-dihydroindol-5-yl | O | H | —O—CO—CH$_3$ | H | — | — | 1.5 | 103 | 6 |
| I | 4-(N-piperidino) | H | O | H | —O—CO—CH$_3$ | H | — | — | 0.2 | 117 | 0 |
| I | 4-CH$_3$O | H | O | H | —O—CO—CH$_3$ | H | — | — | 0.3 | 119 | 2 |
| I | 4-Me$_2$N | H | O | H | —O—CO—C$_2$H$_5$ | H | — | — | 0.4 | 110 | 4 |
| I | 4-(N-pyrrolidino) | H | O | H | —O—CO—CH$_3$ | H | — | — | 0.4 | 108 | 1 |
| I | 4-Me$_2$N | H | O | H | O—CO—CH$_2$C$_6$H$_5$ | H | — | — | 1.9 | 99 | 16 |
| I | 4-Me$_2$N | H | O | H | —OH | H | — | — | N.D. | 29 | 4 |

TABLE 2-continued

T47D Cell Activity

| | | | | | | | | | | Cell Proliferation | | |
|---|---|---|---|---|---|---|---|---|---|---|---|---|
| Structure | R¹ | R¹² | X | R⁶ | R⁷ | R⁹ | R¹⁰ | R¹¹ | Antagonist EC50 (nm) | % Inhib. | Agonist % Stim. |
| I | 4-Me₂N | H | O | H | —O—CO—C₆H₅ | H | — | — | 6.4 | 69 | 18 |
| I | 1-methylindol-5-yl | H | O | H | —O—CO—CH₃ | H | — | — | 0.7 | 110 | 17 |
| I | 4-Me₂N | 3-F | O | H | —O—CO—CH₃ | H | — | — | 0.7 | 101 | 30 |
| I | 2-dimethylamino-5-pyridyl | H | O | H | —O—CO—CH₃ | H | — | — | 2.9 | 92 | 5 |
| I | 4-Me₂N | H | O | H | —CCH | H | — | — | 0.4 | 101 | 12 |
| I | 4-Me₂N | H | O | H | CH₂—O—CO—CH₃ | H | — | — | 8.9 | 92 | 20 |
| I | 4-Me₂N | H | O | H | —CH₂—OH | H | — | — | N.D. | 23 | 11 |
| I | 4-Me₂N | H | O | H | —CH₂OCH₃ | H | — | — | 0.3 | 106 | 12 |
| I | 4-(N-piperidino) | H | O | H | —O—CO—C₂H₅ | H | — | — | 1.0 | 111 | −16 |
| I | 4-(N-pyrrolidino) | H | O | H | —O—CO—C₂H₅ | H | — | — | 0.9 | 107 | −1 |
| I | 1-methylindol-5-yl | H | O | H | —O—CO—C₂H₅ | H | — | — | 2.4 | 107 | 7 |
| I | 4-Me₂N | H | O | H | COOCH₃ | H | — | — | 0.4 | 92 | 24 |

N.D. not detected

TABLE 3

Progestational Activity

McGinty Assay (Agonist)

| | | | | | | | | | Dose (Micrograms) | | |
|---|---|---|---|---|---|---|---|---|---|---|---|
| | | | | | | | | | 0.3 | 3 | 30 |
| Structure | R¹ | R¹² | X | R⁶ | R⁷ | R⁹ | R¹⁰ | R¹¹ | | McPhail Index | |
| Vehicle | | | | | | | | | 0 | | |
| Progesterone | | | | | | | | | 2.45 +/− 0.14 | | |
| I | 4-Me₂N | H | O | H | C₂H₅ | H | — | — | 0.2 +/− 0.1 | 0.3 +/− 0.2 | 0.3 +/− 0.26 |
| I | 1-methyl-2,3-dihydroindol-5-yl | H | O | H | —O—CO—CH₃ | H | — | — | 0.6 +/− 0.1 | 0.2 +/− 0.1 | 0.2 +/− 0.1 |
| I | 4-(N-piperidino) | H | O | H | —O—CO—CH₃ | H | — | — | 0.1 +/− 0.1 | 0 +/− 0 | 0.2 +/− 0.1 |
| I | 4-CH₃O | H | O | H | —O—CO—CH₃ | H | — | — | 1.5 +/− 0.2 | 1.5 +/− 0.6 | 1.5 +/− 0.7 |
| I | 4-Me₂N | H | O | H | —O—CO—C₂H₅ | H | — | — | 0 +/− 0 | 0 +/− 0 | 0 +/− 0 |
| I | 4-(N-pyrrolidino) | H | O | H | —O—CO—CH₃ | H | — | — | 0 +/− 0 | 0 +/− 0 | 0 +/− 0 |
| I | 4-Me₂N | H | O | H | —O—CO—CH₂C₆H₅ | H | — | — | 0 +/− 0 | 0.1 +/− 0.1 | 0 +/− 0 |
| I | 4-Me₂N | H | O | H | —OH | H | — | — | 0 +/− 0 | 0 +/− 0 | 0 +/− 0 |
| I | 4-Me₂N | H | O | H | —O—CO—C₆H₅ | H | — | — | 0 +/− 0 | 0 +/− 0 | 0 +/− 0 |
| I | 1-methylindol-5-yl | H | O | H | —O—CO—CH₃ | H | — | — | 0 +/− 0 | 0 +/− 0 | 0 +/− 0 |
| I | 4-Me₂N | 3-F | O | H | —O—CO—CH₃ | H | — | — | 2.5 +/− 0.2 | 3.0 +/− 0.3 | 3.6 +/− 0.1 |
| I | 2-dimethylamino-5-pyridyl | H | O | H | —O—CO—CH₃ | H | — | — | 0 +/− 0 | 0 +/− 0 | 0 +/− 0 |
| I | 4-Me₂N | H | O | H | —CCH | H | — | — | 0.1 +/− 0.1 | 0.2 +/− 0.2 | 0.2 +/− 0.2 |
| I | 4-Me₂N | H | O | H | —CH₂—O—CO—CH₃ | H | — | — | 0 +/− 0 | 0.6 +/− 0.2 | 1.0 +/− 0.1 |
| I | 4-Me₂N | H | O | H | —CH₂—OH | H | — | — | 0 +/− 0 | 0 +/− 0 | 0 +/− 0 |
| I | 4-Me₂N | H | O | H | —CH₂OCH₃ | H | — | — | 1.3 +/− 0.5 | 1.8 +/− 0.6 | 1.3 +/− 0.8 |
| I | 4-(N-piperidino) | H | O | H | —O—CO—C₂H₅ | H | — | — | 0 +/− 0 | 0 +/− 0 | 0 +/− 0 |
| I | 4-(N-pyrrolidino) | H | O | H | —O—CO—C₂H₅ | H | — | — | 0 +/− 0 | 0 +/− 0 | 0.1 +/− 0.1 |
| I | 1-methylindol-5-yl | H | O | H | —O—CO—C₂H₅ | H | — | — | 0 +/− 0 | 0 +/− 0 | 0 +/− 0 |
| I | 4-Me₂N | H | O | H | COOCH₃ | H | — | — | 0 +/− 0 | 0 +/− 0 | 0.07 +/− 0.07 |
| II | 4-Me₂N | H | O | H | — | — | H | H | 0 +/− 0 | 0 +/− 0 | 0 +/− 0 |

TABLE 4

Antiprogestational Activity

McGinty Assay (Antagonist)

| | | | | | | | | | Dose (Micrograms) | | |
|---|---|---|---|---|---|---|---|---|---|---|---|
| | | | | | | | | | 0.3 | 3 | 30 |
| Structure | R¹ | R¹² | X | R⁶ | R⁷ | R⁹ | R¹⁰ | R¹¹ | | McPhail Index | |
| Vehicle | | | | | | | | | 0 | | |
| Progesterone (Standard) | | | | | | | | | 2.45 +/− 0.14 | | |
| I | 4-Me₂N | H | O | H | C₂H₅ | H | — | — | 3.0 +/− 0.4 | 0.6 +/− 0.3 | 0.8 +/− 0.3 |
| I | 1-methyl-2,3-dihydroindol-5-yl | H | O | H | —O—CO—CH₃ | H | — | — | 2.9 +/− 0.6 | 1.1 +/− 0.6 | 0.4 +/− 0.1 |
| I | 4-(N-piperidino) | H | O | H | —O—CO—CH₃ | H | — | — | 1.7 +/− 0.8 | 0 +/− 0 | 0.2 +/− 0.1 |
| I | 4-CH₃O | H | O | H | —O—CO—CH₃ | H | — | — | 3.3 +/− 0.2 | 1.7 +/− 0.4 | 1.5 +/− 0.5 |
| I | 4-Me₂N | H | O | H | —O—CO—C₂H₅ | H | — | — | 3.3 +/− 0.3 | 0.17 +/− 0.1 | 0 +/− 0 |
| I | 4-(N-pyrrolidino) | H | O | H | —O—CO—CH₃ | H | — | — | 3.0 +/− 0.4 | 0.6 +/− 0.2 | 0 +/− 0 |

TABLE 4-continued

Antiprogestational Activity

| McGinty Assay (Antagonist) Structure | $R^1$ | $R^{12}$ | X | $R^6$ | $R^7$ | $R^9$ | $R^{10}$ | $R^{11}$ | Dose (Micrograms) 0.3 | 3 McPhail Index | 30 |
|---|---|---|---|---|---|---|---|---|---|---|---|
| I | 4-Me$_2$N | H | O | H | —O—CO—CH$_2$C$_6$H$_5$ | H | — | — | 2.3 +/− 0.3 | 3.1 +/− 0.1 | 1.2 +/− 0.2 |
| I | 4-Me$_2$N | H | O | H | —OH | H | — | — | 2.8 +/− 0 | 2.4 +/− 0.4 | 2.1 +/− 0.4 |
| I | 4-Me$_2$N | H | O | H | —O—CO—C$_6$H$_5$ | H | — | — | 2.5 +/− 0.5 | 2.5 +/− 0.3 | 0 +/− 0 |
| I | 1-methylindol-5-yl | | O | H | —O—CO—CH$_3$ | H | — | — | 2.7 +/− 0.1 | 0.5 +/− 0.2 | 0 +/− 0 |
| I | 4-Me$_2$N | 3-F | O | H | —O—CO—CH$_3$ | H | — | — | 3.6 +/− 0.1 | 3.3 +/− 0.3 | 2.8 +/− 0.3 |
| I | 2-dimethylamino-5-pyridyl | | O | H | —O—CO—CH$_3$ | H | — | — | 2.5 +/− 0.3 | 1.8 +/− 0.3 | 0.1 +/− 0.1 |
| I | 4-Me$_2$N | H | O | H | —CCH | H | — | — | 3.3 +/− 0.3 | 0.6 +/− 0.1 | 0 +/− 0 |
| I | 4-Me$_2$N | H | O | H | —CH$_2$—O—CO—CH$_3$ | H | — | — | 3.4 +/− 0.1 | 2.6 +/− 0.2 | 2.0 +/− 0.2 |
| I | 4-Me$_2$N | H | O | H | —CH$_2$—OH | H | — | — | 2.9 +/− 0.5 | 2.8 +/− 0.2 | 2.7 +/− 0.2 |
| I | 4-Me$_2$N | H | O | H | —CH$_2$OCH$_3$ | H | — | — | 3.2 +/− 0.1 | 1.7 +/− 0.8 | 1.7 +/− 0.3 |
| I | 4-(N-piperidino) | H | O | H | —O—CO—C$_2$H$_5$ | H | — | — | 1.5 +/− 0.2 | 0.1 +/− 0.1 | 0 +/− 0 |
| I | 4-(N-pyrrolidino) | H | O | H | —O—CO—C$_2$H$_5$ | H | — | — | 1.6 +/− 0.3 | 1.6 +/− 0.3 | 0 +/− 0 |
| I | 1-methylindol-5-yl | | O | H | —O—CO—C$_2$H$_5$ | H | — | — | 3.1 +/− 0.3 | 1.5 +/− 0.7 | 0.1 +/− 0.1 |
| I | 4-Me$_2$N | H | O | H | COOCH$_3$ | H | — | — | 2.2 +/− 0.2 | 0.2 +/− 0.1 | 0.1 +/− 0.0 |
| II | 4-Me$_2$N | H | O | H | — | — | H | H | 2.7 +/− 0.4 | 0 +/− 0 | 0 +/− 0 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A hormonal or antihormonal steroid compound of structure I,

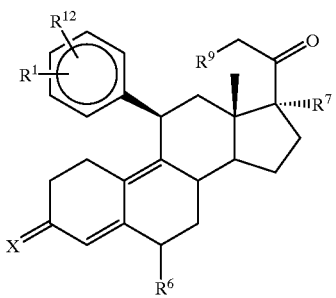

(I)

wherein
$R^1$ is

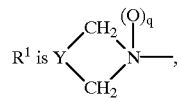

where q is 0 or 1, Y is —(CH$_2$)$_m$— where m is an integer of 0 to 5, optionally substituted;

$R^{12}$ is H or halo;

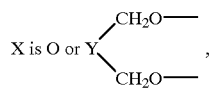

where Y is —(CH$_2$)$_m$— where m is an integer of 0 through 3, $R^6$ is H, CH$_3$, or halogen;

$R^7$ is C$_1$–C$_4$ alkyl, C$_2$–C$_4$ alkenyl, or C$_2$–C$_4$ alkynyl, any of which may be optionally substituted; or $R^7$ is O—CO—$R^8$ or O—$R^8$ where $R^8$ is C$_1$–C$_{18}$ alkyl, C$_2$–C$_{18}$ alkenyl, C$_2$–C18 alkynyl, C$_4$–C$_8$ cycloalkyl, C$_6$–C$_{12}$ aryl, aralkyl, aralkenyl, aralkynyl, heteroaryl, heteroaralkyl, heteroaralkenyl or heteroaralkyl, any of which may be optionally substituted; and $R^9$ is H, lower alkyl, alkenyl or alkynyl, halo, O—CO—$R^8$ or O—$R^8$ where $R^8$ is as defined above, and pharmaceutically acceptable salts thereof.

2. The steroid having structure I of claim 1 wherein $R^1$—Ph is 4-(N-piperidino)phenyl, 4-(N-pyrrolidino)phenyl, 1-methylindol-5-yl or 1-methyl-2,3-dihydroindol-5-yl);

X is O;

$R^6$ is H, CH$_3$, F or Cl;

$R^7$ is H, methyl, ethyl, ethynyl, 1-propynyl, trifluro-1-propynyl, 3-hydroxypropyn-1-yl, propyl, 3-hydroxypropyl, 3-hydroxy-1-propenyl (E- or Z-), acetoxy, propionoxy, benzylcarboxy, benzoyloxy or methoxymethyl; and $R^9$ is H, CH$_3$, acetoxy, fluoro, chloro or methoxy.

3. A steroid of claim 1 selected from the group consisting of:

17α-acetoxy-11β-(4-(N-piperidino)phenyl)-19-norpregna-4,9-diene-3,20-dione, 17α-acetoxy-11β-(4-(N-pyrrolidino)phenyl)-19-norpregna-4,9-diene-3,20-dione, 17α-acetoxy-11β-(1-methylindol-5-yl)-19-norpregna-4,9-diene-3,20-dione, 17α-acetoxy-11β-(1-methyl-2,3-dihydroindol-5-yl)-19-norpregna-4,9-diene-3,20-dione, 11β-(4-(N-piperidino)phenyl)-17α-propionyloxy-19-norpregna-4,9-diene-3,20-dione, 17β-propionyloxy-11β-(4-(N-pyrrolidino)phenyl)-19-norpregna-4,9-diene-3,20-dione, 11β-(1-methylindol-5-yl)-17α-propionyloxy-19-norpregna-4,9-diene-3,20-dione, 11β-(1-methyl-2,3-dihydroindol-5-yl)-17α-propionyloxy-19-norpregna-4,9-diene-3,20-dione and a mixture thereof.

4. A method of therapeutically modifying the activity of progesterone comprising administering a therapeutically effective amount of the compound of claim 1, to a patient in need thereof for a therapeutic purpose.

5. The method of claim 4, wherein said therapeutic purpose is the treatment of endometriosis or uterine fibroids.

6. The method of claim 4, wherein said therapeutic purpose is cervical ripening preparatory to labor and delivery of offspring.

7. The method of claim 4, wherein said therapeutic purpose is the control or regulation of fertility.

8. The method of claim 4, wherein said therapeutic purpose is the treatment of tumors or cancers.

9. The method of claim 4, wherein said therapeutic purpose is hormone replacement therapy.

* * * * *